US012264321B2

(12) United States Patent
Tan et al.

(10) Patent No.: US 12,264,321 B2
(45) **Date of Patent: *Apr. 1, 2025**

(54) Cry1D FOR CONTROLLING CORN EARWORM

(71) Applicant: AGRIGENETICS, INC., Indianapolis, IN (US)

(72) Inventors: Sek Yee Tan, Lincoln, CA (US); Joel J Sheets, San Luis Obispo, CA (US); Todd P Glancy, Fairmount, IN (US); Aaron Todd Woosley, Fishers, IN (US); Sarah E Worden, Johnston, IA (US); Diaa Alabed, Carmel, IN (US); Stephanie Love Burton, Indianapolis, IN (US); Karen C McLaughlin, Indianapolis, IN (US); Kenneth Narva, Zionsville, IN (US); Thomas Meade, Zionsville, IN (US)

(73) Assignee: AGRIGENETICS, INC., Indianapolis, IN (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/469,586

(22) Filed: Sep. 19, 2023

(65) Prior Publication Data

US 2024/0076687 A1 Mar. 7, 2024

Related U.S. Application Data

(63) Continuation of application No. 17/936,908, filed on Sep. 30, 2022, now Pat. No. 11,795,471, which is a continuation of application No. 16/876,756, filed on May 18, 2020, now Pat. No. 11,485,983, which is a continuation of application No. 15/894,267, filed on Feb. 12, 2018, now Pat. No. 10,683,517, which is a continuation of application No. 14/664,307, filed on Mar. 20, 2015, now Pat. No. 9,890,390.

(60) Provisional application No. 61/968,703, filed on Mar. 21, 2014.

(51) Int. Cl.

| | |
|---|---|
| ***C12N 15/82*** | (2006.01) |
| ***A01N 63/23*** | (2020.01) |
| ***A01N 63/50*** | (2020.01) |
| ***C07K 14/325*** | (2006.01) |

(52) U.S. Cl.

CPC ......... *C12N 15/8286* (2013.01); *A01N 63/23* (2020.01); *A01N 63/50* (2020.01); *C07K 14/325* (2013.01); *Y02A 40/146* (2018.01)

(58) Field of Classification Search

None

See application file for complete search history.

(56) References Cited

U.S. PATENT DOCUMENTS

| | | | | |
|---|---|---|---|---|
| 7,511,129 | B2 | 3/2009 | Payne et al. | |
| 8,304,604 | B2 | 11/2012 | Lira et al. | |
| 9,499,835 | B2 | 11/2016 | Meade et al. | |
| 9,796,982 | B2 | 10/2017 | Meade et al. | |
| 9,890,390 | B2 * | 2/2018 | Tan .................... | C12N 15/8286 |
| 10,683,517 | B2 * | 6/2020 | Tan .................... | C12N 15/8286 |
| 11,485,983 | B2 * | 11/2022 | Tan .................... | C12N 15/8286 |
| 11,795,471 | B2 * | 10/2023 | Tan .................... | C12N 15/8286 |
| 2006/0112447 | A1 | 5/2006 | Bogdanova et al. | |
| 2010/0221238 | A1 | 9/2010 | Flexner et al. | |
| 2010/0235951 | A1 | 9/2010 | Van et al. | |
| 2012/0331589 | A1 * | 12/2012 | Meade ............... | C12N 15/8286<br>435/254.2 |
| 2013/0025006 | A1 | 1/2013 | Meade et al. | |
| 2023/0049002 | A1 | 2/2023 | Tan et al. | |

FOREIGN PATENT DOCUMENTS

| | | | |
|---|---|---|---|
| EP | 3119187 | B1 | 4/2020 |
| WO | 9002801 | A2 | 3/1990 |
| WO | 9015139 | A1 | 12/1990 |
| WO | 0026371 | A1 | 5/2000 |
| WO | 2011084629 | A1 | 7/2011 |
| WO | 2011084630 | A1 | 7/2011 |
| WO | 2013134734 | A2 | 9/2013 |
| WO | 2014055881 | A1 | 4/2014 |
| WO | 2016061377 | A2 | 4/2016 |

OTHER PUBLICATIONS

Avilla C., et al., "Toxicity of Several Delta-Endotoxins of Bacillus Thuringiensis against Helicoverpa Armigera (Lepidoptera: Noctuidae) from Spain," Journal of Invertebrate Pathology, Sep. 2005, vol. 90, No. 1, pp. 51-54, XP005100363.

"Common Name: Corn Earworm," Featured Creatures, University of Florida, 2007, 8 Pages, Retrived from URL: http://entnemdept.ufl.edu/creatures/veg/corn_earworm.htm.

"Common Name: Fall Armyworm," Featured Creatures, University of Florida, 2005, 9 Pages, Retrived from URL: http://entnemdept.ufl.edu/creatures/field/fall_armyworm.htm.

Communication from EPO on Oral Proceedings in Opposition Proceeding to EP3119187, dated Dec. 9, 2022, 1 page.

(Continued)

*Primary Examiner* — Anne Kubelik

(57) ABSTRACT

The subject invention relates in part to the surprising discovery that Cry1Da is active against corn earworm (CEW), *Helicoverpa zea* (Boddie). Methods for using Cry1Da in transgenic plants to prevent serious crop damage is described. Leaf and silk bioassays using transgenic maize expressing full length, core toxin region or chimeric Cry1Da demonstrated good insect protection against CEW larvae damage.

3 Claims, 1 Drawing Sheet

Specification includes a Sequence Listing.

(56) References Cited

OTHER PUBLICATIONS

Communication from EPO on Oral Proceedings in Opposition Proceeding to EP3119187, dated Oct. 20, 2022, 2 pages.
Communication of a Notice of Opposition for European Application No. 15764130.9, dated Jan. 22, 2021, 30 pages.
Communication Pursuant to Rule 82(2) EPC in Opposition Proceeding to EP3119187, dated Apr. 21, 2023, 4 pages.
Extended European Search Report for European Application No. 15764130.9, mailed Jul. 20, 2017, 07 Pages.
Extended European Search Report for European Application No. 20167635.0, mailed Sep. 15, 2020, 07 Pages.
Frankenhuyzen K.V., "Insecticidal Activity of Bacillus thuringiensis Crystal Proteins," Journal of Invertebrate Pathology, 2009, vol. 101, No. 1, pp. 1-16, DOI:10.1016/j.jip.2009.02.009, XP026040887.
Hofte H., et al., "Nucleotide Sequence and Deduced Amino Acid Sequence of a New Lepidoptera-specific Crystal Protein Gene from Bacillus Thuringiensis," Nucleic Acids Research, 1990, vol. 18, No. 18, p. 5545, DOI:10.1093/nar/18.18.5545, XP055238596.
Interlocutory Decision in Opposition Proceedings (Art. 101(3)(a) and 106(2) EPC) for European Application No. 3119187, dated Jan. 4, 2023, 57 pages.
International Preliminary Report on Patentability for International Application No. PCT/US2015/021734, mailed Sep. 29, 2016, 07 Pages.
International Search Report and Written Opinion for International Application No. PCT/US2015/021734, mailed Jul. 8, 2015, 09 Pages.
Karim S., et al., "Determination of Receptor Binding Properties of Bacillus Thuringiensis delta-Endotoxins to Cotton Bollworm (*Helicoverpa zea*) and Pink Bollworm (*Pectinophora gossypiella*) Midgut Brush Border Membrane Vesicles," Pesticide Biochemistry and Physiology, Jul. 2000, vol. 67, No. 3, pp. 198-216, doi:10.1006/pest.2000.2491, XP002167866.
Laster M.L., et al., "Search for Hybrid Sterility for Helicoverpa zea in Crosses Between the North American H. zea and H. armigera (Lepidoptera: Noctuidae) from China," Journal of Economic Entomology, Oct. 1995, vol. 88, No. 5, pp. 1288-1291, XP055773085.
Lynch R.E., et al., "Evaluation of Transgenic Sweet Corn Hybrids Expressing CryIA(b) Toxin for Resistance to Corn Earworm and Fall Armyworm (Lepidoptera: Noctuidae)," Journal of Economic Entomology, Feb. 1, 1999, vol. 92, Issue 1, pp. 246-252.
Response to Notice of Opposition in Opposition Proceedings for European Application No. 15764130.9, dated Jun. 11, 2021, 20 pages.
Sequence Alignments Document D13 in Opposition Proceeding for European Application No. 15764130.9, 3 pages.
Submission in Opposition Proceedings for European Application No. 3119187, dated Dec. 2, 2022, 5 pages.
Submission in Opposition Proceedings for European Application No. 3119187, dated Oct. 13, 2022, 68 pages.
Summons to Oral Proceedings and Preliminary Non-Binding Opinion in Opposition Proceedings for European Application No. 15764130.9, dated Oct. 26, 2021, 8 pages.
Tabashnik B.E., et al., "Cross-Resistance of the Diamondback Moth Indicates Altered Interactions with Domain II of Bacillus thuringiensis Toxins," Applied and Environmental Microbiology, Aug. 1996, vol. 62, No. 8, pp. 2839-2844.
UniProt: Database Accession No. P19415, Submitted Nov. 1, 1990, 4 pages.

* cited by examiner

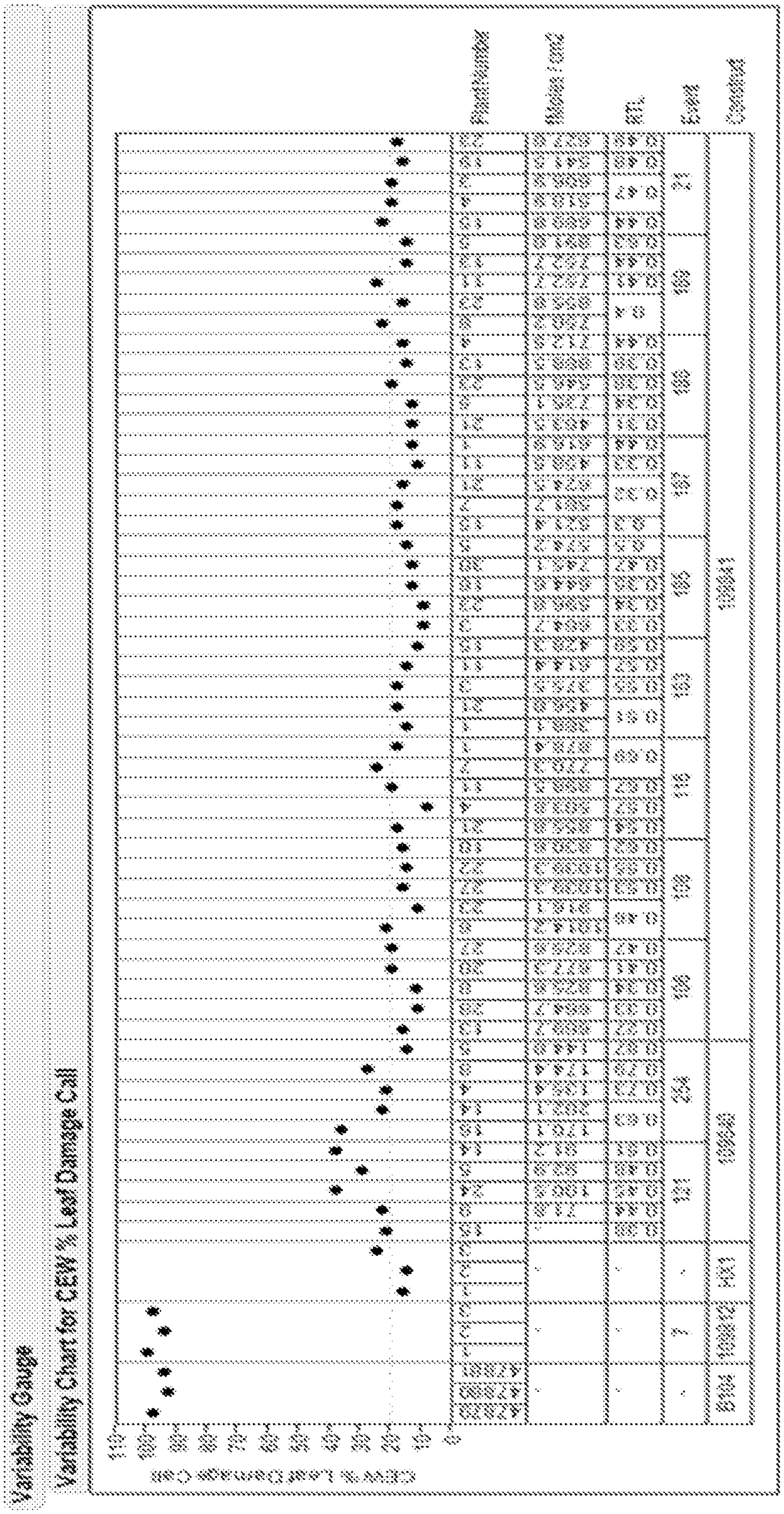
Variability Gauge
Variability Chart for CEW % Leaf Damage Call

Cry1D FOR CONTROLLING CORN EARWORM

CROSS REFERENCE

This application is a continuation of U.S. Non-Provisional application Ser. No. 17/936,908 filed on Sep. 30, 2022, which is a continuation of U.S. Non-Provisional application Ser. No. 16/876,756 filed on May 18, 2020, now U.S. Pat. No. 11,485,983, which is a continuation of U.S. Non-Provisional application Ser. No. 15/894,267 filed on Feb. 12, 2018, now U.S. Pat. No. 10,683,517, which is a continuation of U.S. Non-Provisional application Ser. No. 14/664,307 filed Mar. 20, 2015, now U.S. Pat. No. 9,890,390, which claims benefits of U.S. Provisional Application No. 61/968,703, filed on Mar. 21, 2014. The disclosures of each of which are expressly incorporated herein by reference in their entireties.

REFERENCE TO SEQUENCE LISTING SUBMITTED ELECTRONICALLY

An XML formatted sequence listing having the file name "74266-US-CNT3_SequenceListing.xml" created on Sep. 27, 2022 and having a size of 31,789 bytes is filed in computer readable form concurrently with the specification. The sequence listing comprised in this XML formatted document is part of the specification and is herein incorporated by reference in its entirety.

BACKGROUND

Cry1Da is a known delta-endotoxin produced by certain species of *Bacillus thuringiensis* and was first described in U.S. Pat. No. 5,691,308. More recently has been reported to be inactive against corn earworm (CEW) by two independent peer reviewed papers: Karim et al. (2000) and Frankenhuyzen (2009). Consequently the following surprising and unexpected observations directly refutes these published results and clearly shows that Cry1Da has good insecticidal activity against CEW larvae when the gene is expressed in plants.

BRIEF SUMMARY

The subject invention relates in part to the surprising discovery that Cry1Da is active against corn earworm larvae (CEW), *Helicoverpa zea* (Boddie). Leaf and silk bioassays using transgenic maize expressing a full length, truncated, and chimeric versions of Cry1Da demonstrated good insect protection against CEW larvae damage. Further surprising was that protection of CEW larvae feeding of maize silk was found to be superior in transgenic plants expressing truncated Cry1Da as compared to commercial plants producing Cry1Fa.

CEW is a difficult insect pest to control with *Bacillus thuringiensis* (Bt) proteins, and this is the first described observation where transgenic maize expressing Cry1Da demonstrated biological activity to protect maize silk from feeding damage caused by this insect. Adult CEW moths typically oviposite their eggs on corn silk, and the newly emerging larvae feed on corn silk prior to entering the ear. Thus, having insect protectant activity located in maize silk tissues will provide significant protective effects against feeding damage caused by this significant and destructive pest of maize.

BRIEF DESCRIPTION OF THE FIGURE

Percent leaf damage activity of non-transformed maize (B-104), YFP expressing transgenic maize (109812), HerculexI™ maize (HX1), or transgenic T-1 maize expressing either full length Cry1Da (109840), or truncated Cry1Da (109841) challenged with CEW larvae.

BRIEF DESCRIPTION OF THE SEQUENCES

SEQ ID NO: 1 is a DNA fragment having the DIG-911 coding sequence (CDS)

SEQ ID NO:2 is the amino acid sequence for the DIG-911 protein (Cry1Da2/Cry1Ab chimeric insecticidal toxin, which consists of a core toxin segment of Cry1Da (amino acids 1 to 594, as disclosed in GENBANK Accession No. 176415.1 and U.S. Pat. No. 5,691,308) and a protoxin segment derived from Cry1Ab (DIG-911 amino acids 595 to 1139), essentially as disclosed in GENBANK Accession No. AFK79795.1)

SEQ ID NO:3 is a DNA fragment having the DIG-180 coding sequence (CDS) SEQ ID NO:4 is the DIG-180 (Cry1Fa2) protein.

SEQ ID NO:5 is a Gateway® (INVITROGEN) entry vector pDAB109825 comprising a maize-optimized coding sequence (SEQ ID NO:5) that encodes a Cry1Da2 core toxin insecticidal protein (SEQ ID NO:6).

SEQ ID NO:6 is the Cry1Da2 core toxin insecticidal protein.

SEQ ID NO:7 is a primer for AAD-1; see Table 2

SEQ ID NO:8 is a primer for AAD-1

SEQ ID NO:9 is a probe for AAD-1

SEQ ID NO:10 is a primer for the spectinomycin resistance gene

SEQ ID NO:11 is a primer for the spectinomycin resistance gene

SEQ ID NO:12 is a probe for the spectinomycin resistance gene

SEQ ID NO:13 is a primer for the maize invertase gene

SEQ ID NO: 14 is a primer for the maize invertase gene

SEQ ID NO: 15 is a probe for the maize invertase gene

DETAILED DESCRIPTION

The subject invention relates in part to the surprising discovery that Cry1Da is active against corn earworm larvae (CEW), *Helicoverpa zea* (Boddie). Bioassay results from in vitro diet bioassays showed Cry1Da/Cry1Ab protoxin chimera results in significant growth inhibition and mortality to CEW larvae. A Cry1Da insecticidal protein or toxin is any insecticidal protein comprising the core toxin set forth in SEQ ID NO:6 or variants thereof. Such variants have at least 95% sequence identity to SEQ ID NO:6, preferable 99% sequence identity to SEQ ID NO: 6.

Leaf and silk bioassays using transgenic maize expressing a truncated version of Cry1Da demonstrated good insect protection against CEW larvae damage. Comparable leaf protection against CEW feeding was observed in both transgenic maize plants expressing truncated Cry1Da and the commercial Herculex® I (HX1) product expressing Cry1Fa.

Surprisingly, protection of CEW larvae feeding of maize silk was found to be superior in transgenic plants expressing truncated Cry1Da as compared to HX1 plants. Insects feeding on silk tissue from transgenic maize expressing truncated Cry1Da experienced mortality (~25%), which was numerically better than observed for insects feeding on silk tissue from HX1 plants (<10%).

CEW is a difficult insect pest to control with *Bacillus thuringiensis* (Bt) proteins, and this is the first described observation where transgenic maize expressing Cry1Da demonstrated biological activity to protect maize silk from feeding damage caused by this insect. Adult CEW moths typically oviposite their eggs on corn silk and the newly emerging larvae feed on corn silk prior to entering the ear. Thus, having insect protectant activity located in maize silk tissues will provide significant protective effects against feeding damage caused by this significant and destructive pest of maize. Deployment options of the subject invention include the use of Cry1Da proteins in geographical regions, including soybean- and corn-growing regions where CEW are present and problematic.

The data presented herein demonstrate that Cry1Da is an excellent protein to control CEW through silk tissues compared to Herculex 1®. As used herein, the terms "control" and "controlling" include growth inhibition and/or mortality.

A Cry1Da/Cry1Ab protoxin chimera is shown herein to have insecticidal activity against *H. zea* in diet insect bioassays. When the truncated form of Cry1Da was expressed in transgenic maize, it protected the plants from leaf and silk feeding damage caused by either CEW or fall armyworm (FAW), *Spodoptera frugiperda*. These results are surprising as Cry1Da was previously reported to not be active against CEW (Karim, 2000) and only active against FAW (Van Frankenhuyzen, 2009). The Cry1Da insecticidal protein is known; however, this invention is a novel and unexpected use of Cry1Da for preventing serious CEW damage to plants, especially crop plants.

*Helicoverpa zea* has a polyphagous larval feeding habit. It feeds preferably on reproductive structures and growing tissues that are nitrogen-rich, such as the maize silk, ear, cob and tassel, cotton boll and bud, as well as soybean pod. It is a very significant insect (pest to crops) because of plant damage directly impacting the crop yield. Apart from maize, Cry1Da has utility to control this insect species in high value crops such as cotton and soybeans, as well as vegetables such as tomatoes.

Insect resistance management (IRM) describes farming practices used to reduce the potential for insect pests to become resistant to a pesticide. IRM is of great importance relative to the use of Cry toxins in major crop plants because insect resistance poses numerous threats to the use Cry toxins in transgenic crops. Specific IRM strategies, such as the high dose and structured refuge have the ability to diminish the likelihood that insects will develop resistance to certain Cry toxins. Effective IRM practices can reduce the risk of resistance development.

On its website, the United States Environmental Protection Agency (epa.gov/oppbppd1/biopesticides/pips/bt_corn_refuge_2006.htm) publishes the following requirements for providing refuges made up of non Cry toxin-bearing plants for use with transgenic crops producing a single Cry toxin active against target pests.

"The specific structured requirements for corn borer-protected Bt (Cry1Ab or Cry 1F) corn products are as follows:

Structured refuges:

20% non-Lepidopteran Bt corn refuge in Corn Belt;

50% non-Lepidopteran Bt refuge in Cotton Belt

Blocks

Internal (i.e., within the Bt field)

External (i.e., separate fields within ½ mile (½ mile if possible) of the Bt field to maximize random mating)

In-field Strips

Strips must be at least 4 rows wide (preferably 6 rows) to reduce the effects of larval movement"

In addition, the National Corn Growers Association, on its website: (ncga.com/insect-resistance-management-fact-sheet-bt-corn) also provides similar guidance regarding the refuge requirements. For example:

"Requirements of the Corn Borer IRM:

Plant at least 20% of your corn acres to refuge hybrids

In cotton producing regions, refuge must be 50%

Must be planted within ½ mile of the refuge hybrids

Refuge can be planted as strips within the Bt field; the refuge strips must be at least 4 rows wide Refuge may be treated with conventional pesticides only if economic thresholds are reached for target insect Bt-based sprayable insecticides cannot be used on the refuge corn Appropriate refuge must be planted on every farm with Bt corn"

There are various ways of providing the IRM effects of a refuge, including various geometric planting patterns in the fields (as mentioned above) and in-bag seed mixtures, as discussed further by Roush et al. (supra), and U.S. Pat. No. 6,551,962.

Insect toxins, and insect active variants In addition to the specifically exemplified genes and proteins as discussed herein, included are insecticidally active variants. By the term "variant", applicants intend to include fragments, certain deletion and insertion mutants, and certain fusion proteins. The Cry1Da protein is a classic three-domain Cry toxin. As a preface to describing variants of the Cry1Da insect toxin that are included in the invention, it will be useful to briefly review the architecture of three-domain Cry toxins in general and of the Cry1Da insect toxin.

A majority of *Bacillus thuringiensis* delta-endotoxin crystal protein molecules are composed of two functional segments. The protease-resistant core toxin is the first segment and corresponds to about the first half of the protein molecule. The full ~ 130 kDa protoxin molecule is rapidly processed to the resistant core segment by proteases in the insect gut. The segment that is deleted by this processing will be referred to herein as the "protoxin segment." The protoxin segment is believed to participate in toxin crystal formation (Arvidson et al., (1989). The protoxin segment may thus convey a partial insect specificity for the toxin by limiting the accessibility of the core to the insect by reducing the protease processing of the toxin molecule (Haider et al., (1986) or by reducing toxin solubility (Aronson et al., (1991). B.t. toxins, even within a certain class, vary to some extent in length and in the precise location of the transition from the core toxin portion to protoxin portion. The transition from core toxin portion to protoxin portion will typically occur at between about 50% to about 60% of the full length toxin.

Three dimensional crystal structures have been determined for Cry1Aa1, Cry2Aa1, Cry3Aa1, Cry3Bb1, Cry4Aa, Cry4Ba and Cry8Ea1. These structures for the core toxins are remarkably similar and are comprised of three distinct domains (reviewed in de Maagd et al., 2003).

Insect toxin variants created by making a limited number of amino acid deletions, substitutions, or additions Amino acid deletions, substitutions, and additions to the exemplified amino acid sequences can readily be made in a sequential manner and the effects of such variations on insecticidal activity can be tested by bioassay. Provided the number of changes is limited in number, such testing does not involve unreasonable experimentation. The invention includes insecticidally active variants of the core toxin in which up to 10, up to 15, or up to 20 amino acid additions, deletions, or substitutions have been made.

Included are Cry1Da insecticidally active variants that are, including those having a core toxin segment that is, at least 95%, 96%, 97%, 98%, or 99% identical to an exemplified amino acid sequence as used herein. Also included are similar active proteins having at least 90%, 91%, 92%, 93%, or 94% identity with an exemplified sequence.

According to official nomenclature procedures, Cry and B.t. nomenclature is based on boundaries of approximately 95% (Cry1Da's, for example), 78% (Cry1D's), and 45% (Cry1's) sequence identity, per "Revision of the Nomenclature for the *Bacillus thuringiensis* Pesticidal Crystal Proteins," N. Crickmore, D. R. Zeigler, J. Feitelson, E. Schnepf, J. Van Rie, D. Lereclus, J. Baum, and D. H. Dean. Microbiology and Molecular Biology Reviews (1998) Vol 62:807-813.

Variants may be made by making random mutations or the variants may be designed. In the case of designed mutants, there is a high probability of generating variants with similar activity to the native toxin when amino acid identity is maintained in critical regions of the toxin which account for biological activity or are involved in the determination of three-dimensional configuration which ultimately is responsible for the biological activity. A high probability of retaining activity will also occur if substitutions are conservative. Amino acids may be placed in the following classes: nonpolar, uncharged polar, basic, and acidic. Conservative substitutions whereby an amino acid of one class is replaced with another amino acid of the same type are least likely to materially alter the biological activity of the variant. The following lists of examples of amino acids belonging to each class.

| Class of Amino Acid | Examples of Amino Acids |
|---|---|
| Nonpolar Side Chains | Ala, Val, Leu, lie, Pro, Met, Phe, Trp |
| Uncharged Polar Side Chains | Gly, Ser, Thr, Cys, Tyr, Asn, Gin |
| Acidic Side Chains | Asp, Glu |
| Basic Side Chains | Lys, Arg, His |
| Beta-branched Side Chains | Thr, Val, lie |
| Aromatic Side Chains | Tyr, Phe, Trp, His |

In some instances, non-conservative substitutions can also be made. The critical factor is that these substitutions must not significantly detract from the biological activity of the toxin. Variants include polypeptides that differ in amino acid sequence due to mutagenesis. Variant proteins encompassed by the present invention are biologically active, that is they continue to possess the desired biological activity of the native protein, that is, retaining pesticidal activity.

Variant proteins can also be designed that differ at the sequence level but that retain the same or similar overall essential three-dimensional structure, surface charge distribution, and the like. See e.g. U.S. Pat. No. 7,058,515; Larson et al., (2002); Stemmer (1994a, 1994b, 1995); and Crameri et al., (1996a, 1996b, 1997).

Nucleic Acids Isolated nucleic acids encoding Cry1Da insect toxins are one aspect of the present invention. This includes the subject novel uses of nucleic acids encoding SEQ ID NO: 2, SEQ ID NO:4, and SEQ ID NO:6, and complements thereof, as well as other nucleic acids that encode insecticidally active variants. By "isolated" applicants mean that the nucleic acid molecules have been removed from their native environment and have been placed in a different environment by the hand of man. Because of the redundancy of the genetic code, a variety of different DNA sequences can encode the amino acid sequences disclosed herein. It is well within the skill of a person trained in the art to create these alternative DNA sequences encoding the same, or essentially the same, toxins.

Coding sequences of the subject invention can be operably linked to a heterologous promoter, including a non-B.t. promoter. Such sequences can be included in expression constructs, transformation cassettes, and expression cassettes including those as present reproducibly in a plant genome, for example.

Gene synthesis Genes encoding the improved Cry proteins described herein can be made by a variety of methods well-known in the art. For example, synthetic gene segments and synthetic genes can be made by phosphite tri-ester and phosphoramidite chemistry (Caruthers et al, 1987), and commercial vendors are available to perform gene synthesis on demand. Full-length genes can be assembled in a variety of ways including, for example, by ligation of restriction fragments or polymerase chain reaction assembly of overlapping oligonucleotides (Stewart and Burgin, 2005). Further, terminal gene deletions can be made by PCR amplification using site-specific terminal oligonucleotides.

Nucleic acids encoding Cry1Da insect toxins can be made for example, by synthetic construction by methods currently practiced by any of several commercial suppliers. (See for example, U.S. Pat. No. 7,482,119 B2). These genes, or portions or variants thereof, may also be constructed synthetically, for example, by use of a gene synthesizer and the design methods of, for example, U.S. Pat. No. 5,380,831. Alternatively, variations of synthetic or naturally occurring genes may be readily constructed using standard molecular biological techniques for making point mutations. Fragments of these genes can also be made using commercially available exonucleases or endonucleases according to standard procedures. For example, enzymes such as Bal31 or site-directed mutagenesis can be used to systematically cut off nucleotides from the ends of these genes. Also, gene fragments which encode active toxin fragments may be obtained using a variety of restriction enzymes.

Given the amino acid sequence for a Cry1Da insect toxin, a coding sequence can be designed by reverse translating the amino acid sequence using codons preferred by the intended host, and then refining the sequence using alternative codons to remove sequences that might cause problems and provide periodic stop codons to eliminate long open coding sequences in the non-coding reading frames.

Quantifying Sequence Identity To determine the percent identity of two amino acid sequences or of two nucleic acid sequences, the sequences are aligned for optimal comparison purposes. The percent identity between the two sequences is a function of the number of identical positions shared by the sequences (i.e. percent identity=number of identical positions/total number of positions (e.g. overlapping positions)×100). In one embodiment, the two sequences are the same length. The percent identity between two sequences can be determined using techniques similar to those described below, with or without allowing gaps. In calculating percent identity, typically exact matches are counted.

The determination of percent identity between two sequences can be accomplished using a mathematical algorithm. A nonlimiting example of such an algorithm is that of Altschul et al. (1990), and Karlin and Altschul (1990), modified as in Karlin and Altschul (1993), and incorporated into the BLASTN and BLASTX programs. BLAST searches may be conveniently used to identify sequences homologous (similar) to a query sequence in nucleic or protein databases. BLASTN searches can be performed, (score=100, word length=12) to identify nucleotide sequences having homology to claimed nucleic acid molecules of the invention. BLASTX searches can be performed (score=50, word length=3) to identify amino acid sequences having homology to claimed insecticidal protein molecules of the invention.

Gapped BLAST Altschul et al., (1997) can be utilized to obtain gapped alignments for comparison purposes, Alternatively, PSI-Blast can be used to perform an iterated search that detects distant relationships between molecules Altschul et al., (1997). When utilizing BLAST, Gapped BLAST, and PSI-Blast programs, the default parameters of the respective programs can be used. See www.ncbi.nlm.nih.gov.

A non-limiting example of a mathematical algorithm utilized for the comparison of sequences is the ClustalW algorithm (Thompson et al., (1994). ClustalW compares sequences and aligns the entirety of the amino acid or DNA sequence, and thus can provide data about the sequence conservation of the entire amino acid sequence or nucleotide sequence. The ClustalW algorithm is used in several commercially available DNA/amino acid analysis software packages, such as the ALIGNX module of the Vector NTI Program Suite (Invitrogen, Inc., Carlsbad, CA). When aligning amino acid sequences with ALIGNX, one may conveniently use the default settings with a Gap open penalty of 10, a Gap extend penalty of 0.1 and the blosum63mt2 comparison matrix to assess the percent amino acid similarity (consensus) or identity between the two sequences. When aligning DNA sequences with ALIGNX, one may conveniently use the default settings with a Gap open penalty of 15, a Gap extend penalty of 6.6 and the swgapdnamt comparison matrix to assess the percent identity between the two sequences.

Another non-limiting example of a mathematical algorithm utilized for the comparison of sequences is that of Myers and Miller (1988). Such an algorithm is incorporated into the wSTRETCHER program, which is part of the wEMBOSS sequence alignment software package (available at http://emboss.sourceforge.net/). wSTRETCHER calculates an optimal global alignment of two sequences using a modification of the classic dynamic programming algorithm which uses linear space. The substitution matrix, gap insertion penalty and gap extension penalties used to calculate the alignment may be specified. When utilizing the wSTRETCHER program for comparing nucleotide sequences, a Gap open penalty of 16 and a Gap extend penalty of 4 can be used with the scoring matrix file EDNAFULL. When used for comparing amino acid sequences, a Gap open penalty of 12 and a Gap extend penalty of 2 can be used with the EBLOSUM62 scoring matrix file.

A further non-limiting example of a mathematical algorithm utilized for the comparison of sequences is that of Needleman and Wunsch (1970), which is incorporated in the sequence alignment software packages GAP Version 10 and wNEEDLE (http://emboss.sourceforge.net/). GAP Version 10 may be used to determine sequence identity or similarity using the following parameters: for a nucleotide sequence, % identity and % similarity are found using GAP Weight of 50 and Length Weight of 3, and the nwsgapdna.cmp scoring matrix. For amino acid sequence comparison, % identity or % similarity are determined using GAP weight of 8 and length weight of 2, and the BLOSUM62 scoring program.

wNEEDLE reads two input sequences, finds the optimum alignment (including gaps) along their entire length, and writes their optimal global sequence alignment to file. The algorithm explores all possible alignments and chooses the best, using .a scoring matrix that contains values for every possible residue or nucleotide match. wNEEDLE finds the alignment with the maximum possible score, where the score of an alignment is equal to the sum of the matches taken from the scoring matrix, minus penalties arising from opening and extending gaps in the aligned sequences. The substitution matrix and gap opening and extension penalties are user-specified. When amino acid sequences are compared, a default Gap open penalty of 10, a Gap extend penalty of 0.5, and the EBLOSUM62 comparison matrix are used. When DNA sequences are compared using wNEEDLE, a Gap open penalty of 10, a Gap extend penalty of 0.5, and the EDNAFULL comparison matrix are used.

Equivalent programs may also be used. By "equivalent program" is intended any sequence comparison program that, for any two sequences in question, generates an alignment having identical nucleotide or amino acid residue matches and an identical percent sequence identity when compared to the corresponding alignment generated by ALIGNX, wNEEDLE, or wSTRETCHER. The % identity is the percentage of identical matches between the two sequences over the reported aligned region (including any gaps in the length) and the % similarity is the percentage of matches between the two sequences over the reported aligned region (including any gaps in the length).

Alignment may also be performed manually by inspection.

Recombinant hosts The insect toxin-encoding genes of the subject invention can be introduced into a wide variety of microbial or plant hosts. Expression of the insect toxin gene results, directly or indirectly, in the intracellular production and maintenance of the pesticidal protein. With suitable microbial hosts, e.g. *Pseudomonas*, the microbes can be applied to the environment of the pest, where they will proliferate and be ingested. The result is a control of the pest. Alternatively, the microbe hosting the insect toxin gene can be treated under conditions that prolong the activity of the toxin and stabilize the cell. The treated cell, which retains the toxic activity, then can be applied to the environment of the target pest. Non-regenerable/non-totipotent plant cells from a plant of the subject invention (comprising at least one of the subject Cry toxin genes) are included within the subject invention.

Where the B.t. toxin gene is introduced via a suitable vector into a microbial host, and said host is applied to the environment in a living state, it is essential that certain host microbes be used. Microorganism hosts are selected which are known to occupy the "phytosphere" (phylloplane, phyllosphere, rhizosphere, and/or rhizoplane) of one or more crops of interest. These microorganisms are selected so as to be capable of successfully competing in the particular environment (crop and other insect habitats) with the wild-type indigenous microorganisms, provide for stable maintenance and expression of the gene expressing the polypeptide pesticide, and, desirably, provide for improved protection of the pesticide from environmental degradation and inactivation.

A large number of microorganisms are known to inhabit the phylloplane (the surface of the plant leaves) and/or the rhizosphere (the soil surrounding plant roots) of a wide variety of important crops. These microorganisms include bacteria, algae, and fungi. Of particular interest are microorganisms, such as bacteria, e.g. genera *Pseudomonas,*

*Erwinia, Serratia, Klebsiella, Xanthomonas, Streptomyces, Rhizobium, Sinorhizobium, Rhodopseudomonas, Methylophilius, Agrobacterium, Acetobacter, Lactobacillus, Arthrobacter, Azotobacter, Leuconostoc*, and *Alcaligenes*; fungi, particularly yeast, e.g. genera *Saccharomyces, Cryptococcus, Kluyveromyces, Sporobolomyces, Rhodotorula*, and *Aureobasidium*. Of particular interest are such phytosphere bacterial species as *Pseudomonas syringae, Pseudomonas fluorescens, Serratia marcescens, Acetobacter xylinum, Agrobacterium tumefaciens, Agrobacterium radiobacter, Rhodopseudomonas spheroides, Xanthomonas campestris, Sinorhizobium meliloti* (formerly *Rhizobium meliloti*), *Alcaligenes eutrophus*, and *Azotobacter vinelandii*; and phytosphere yeast species such as *Rhodotorula rubra, R. glutinis, R. marina, R. aurantiaca, Cryptococcus albidus, C. diffluens, C. laurentii, Saccharomyces rosei, S. pretoriensis, S. cerevisiae, Sporobolomyces roseus, S. odorus, Kluyveromyces veronae*, and *Aureobasidium* pollulans. Of particular interest are the pigmented microorganisms.

Methods of controlling insect pests. When an insect comes into contact with an effective amount of toxin delivered via transgenic plant expression, formulated protein compositions(s), sprayable protein composition(s), a bait matrix or other delivery system, the results are typically death of the insect, or the insects do not feed upon the source which makes the toxins available to the insects.

The subject protein toxins can be "applied" or provided to contact the target insects in a variety of ways. For example, transgenic plants (wherein the protein is produced by and present in the plant) can be used and are well-known in the art. Expression of the toxin genes can also be achieved selectively in specific tissues of the plants, such as the roots, leaves, etc. This can be accomplished via the use of tissue-specific promoters, for example. Spray-on applications are another example and are also known in the art. The subject proteins can be appropriately formulated for the desired end use, and then sprayed (or otherwise applied) onto the plant and/or around the plant/to the vicinity of the plant to be protected-before an infestation is discovered, after target insects are discovered, both before and after, and the like. Bait granules, for example, can also be used and are known in the art.

Transgenic plants. The subject proteins can be used to protect practically any type of plant from damage by an insect pest. Examples of such plants include maize, sunflower, soybean, cotton, canola, rice, sorghum, wheat, barley, vegetables, ornamentals, peppers (including hot peppers), sugar beets, fruit, and turf, to name but a few. Methods for transforming plants are well known in the art, and illustrative transformation methods are described in the Examples.

A preferred embodiment of the subject invention is the transformation of plants with genes encoding the subject insecticidal protein or its variants. The transformed plants are resistant to attack by an insect target pest by virtue of the presence of controlling amounts of the subject insecticidal protein or its variants in the cells of the transformed plant. By incorporating genetic material that encodes the insecticidal properties of the B.t. insecticidal toxins into the genome of a plant eaten by a particular insect pest, the adult or larvae would die after consuming the food plant. Numerous members of the monocotyledonous and dicotyledonous classifications have been transformed. Transgenic agronomic crops as well as fruits and vegetables are of commercial interest. Such crops include but are not limited to maize, rice, soybeans, canola, sunflower, alfalfa, sorghum, wheat, cotton, peanuts, tomatoes, potatoes, and the like.

Several techniques exist for introducing foreign genetic material into plant cells, and for obtaining plants that stably maintain and express the introduced gene. Such techniques include acceleration of genetic material coated onto microparticles directly into cells (U.S. Pat. Nos. 4,945,050 and 5,141,131). Plants may be transformed using *Agrobacterium* technology, see U.S. Pat. Nos. 5,177,010, 5,104,310, European Patent Application No. 0131624B1, European Patent Application No. 120516, European Patent Application No. 159418B1, European Patent Application No. 176112, U.S. Pat. Nos. 5,149,645, 5,469,976, 5,464,763, 4,940,838, 4,693,976, European Patent Application No. 116718, European Patent Application No. 290799, European Patent Application No. 320500, European Patent Application No. 604662, European Patent Application No. 627752, European Patent Application No. 0267159, European Patent Application No. 0292435, U.S. Pat. Nos. 5,231,019, 5,463,174, 4,762,785, 5,004,863, and U.S. Pat. No. 5,159,135. Other transformation technology includes WHISKERS™ technology, see U.S. Pat. Nos. 5,302,523 and 5,464,765. Electroporation technology has also been used to transform plants, see WO 87/06614, U.S. Pat. Nos. 5,472,869, 5,384,253, WO 9209696, and WO 9321335. All of these transformation patents and publications are incorporated by reference. In addition to numerous technologies for transforming plants, the type of tissue which is contacted with the foreign genes may vary as well. Such tissue would include but would not be limited to embryogenic tissue, callus tissue type I and II, hypocotyl, meristem, and the like. Almost all plant tissues may be transformed during dedifferentiation using appropriate techniques within the skill of an artisan.

Genes encoding Cry1Da insecticidal toxins can be inserted into plant cells using a variety of techniques which are well known in the art as disclosed above. For example, a large number of cloning vectors comprising a marker that permits selection of the transformed microbial cells and a replication system functional in *Escherichia coli* are available for preparation and modification of foreign genes for insertion into higher plants. Such manipulations may include, for example, the insertion of mutations, truncations, additions, or substitutions as desired for the intended use. The vectors comprise, for example, pBR322, pUC series, M13mp series, pACYC184, etc. Accordingly, the sequence encoding the Cry protein or variants can be inserted into the vector at a suitable restriction site. The resulting plasmid is used for transformation of *E. coli*, the cells of which are cultivated in a suitable nutrient medium, then harvested and lysed so that workable quantities of the plasmid are recovered. Sequence analysis, restriction fragment analysis, electrophoresis, and other biochemical-molecular biological methods are generally carried out as methods of analysis. After each manipulation, the DNA sequence used can be cleaved and joined to the next DNA sequence. Each manipulated DNA sequence can be cloned in the same or other plasmids.

The use of T-DNA-containing vectors for the transformation of plant cells has been intensively researched and sufficiently described in European Patent Application No. 120516; Lee and Gelvin (2008), Fraley et al., (1986), and An et al., (1985), and is well established in the field.

Once the inserted DNA has been integrated into the plant genome, it is relatively stable throughout subsequent generations. The vector used to transform the plant cell normally contains a selectable marker gene encoding a protein that confers on the transformed plant cells resistance to a herbicide or an antibiotic, such as bialaphos, kanamycin, G418, bleomycin, or hygromycin, inter alia. The individually employed selectable marker gene should accordingly permit the selection of transformed cells while the growth of cells that do not contain the inserted DNA is suppressed by the selective compound.

A large number of techniques are available for inserting DNA into a host plant cell. Those techniques include transformation with T-DNA delivered by *Agrobacterium tumefaciens* or *Agrobacterium rhizogenes* as the transformation agent. Additionally, fusion of plant protoplasts with liposomes containing the DNA to be delivered, direct injection of the DNA, biolistics transformation (microparticle bombardment), or electroporation, as well as other possible methods, may be employed.

In a preferred embodiment of the subject invention, plants will be transformed with genes wherein the codon usage of the protein coding region has been optimized for plants. See, for example, U.S. Pat. No. 5,380,831, which is hereby incorporated by reference. Also, advantageously, plants encoding a truncated toxin will be used. The truncated toxin typically will encode about 55% to about 80% of the full length toxin. Methods for creating synthetic B.t. genes for use in plants are known in the art (Stewart 2007).

Regardless of transformation technique, the gene is preferably incorporated into a gene transfer vector adapted to express the B.t. insecticidal toxin genes and variants in the plant cell by including in the vector a plant promoter. In addition to plant promoters, promoters from a variety of sources can be used efficiently in plant cells to express foreign genes. For example, promoters of bacterial origin, such as the octopine synthase promoter, the nopaline synthase promoter, the mannopine synthase promoter; promoters of viral origin, such as the 35S and 19S promoters of cauliflower mosaic virus, and the like may be used. Plant promoters include, but are not limited to ribulose-1,6-bisphosphate (RUBP) carboxylase small subunit (ssu), beta-conglycinin promoter, phaseolin promoter, ADH (alcohol dehydrogenase) promoter, heat-shock promoters, ADF (actin depolymerization factor) promoter, and tissue specific promoters. Promoters may also contain certain enhancer sequence elements that may improve the transcription efficiency. Typical enhancers include but are not limited to ADH1-intron 1 and ADH1-intron 6. Constitutive promoters may be used. Constitutive promoters direct continuous gene expression in nearly all cells types and at nearly all times (e.g., actin, ubiquitin, CaMV 35S). Tissue specific promoters are responsible for gene expression in specific cell or tissue types, such as the leaves or seeds (e.g., zein, oleosin, napin, ACP (Acyl Carrier Protein)), and these promoters may also be used. Promoters may also be used that are active during a certain stage of the plants' development as well as active in specific plant tissues and organs. Examples of such promoters include but are not limited to promoters that are root specific, pollen-specific, embryo specific, corn silk specific, cotton fiber specific, seed endosperm specific, phloem specific, and the like.

Under certain circumstances it may be desirable to use an inducible promoter. An inducible promoter is responsible for expression of genes in response to a specific signal, such as: physical stimulus (e.g. heat shock genes); light (e.g. RUBP carboxylase); hormone (e.g. glucocorticoid); antibiotic (e.g. tetracycline); metabolites; and stress (e.g. drought). Other desirable transcription and translation elements that function in plants may be used, such as 5' untranslated leader sequences, RNA transcription termination sequences and poly-adenylate addition signal sequences. Numerous plant-specific gene transfer vectors are known to the art.

Transgenic crops containing insect resistance (IR) traits are prevalent in corn and cotton plants throughout North America, and usage of these traits is expanding globally. Commercial transgenic crops combining IR and herbicide tolerance (HT) traits have been developed by multiple seed companies. These include combinations of IR traits conferred by B.t. insecticidal proteins and HT traits such as tolerance to Acetolactate Synthase (ALS) inhibitors such as sulfonylureas, imidazolinones, triazolopyrimidine, sulfonanilides, and the like, Glutamine Synthetase (GS) inhibitors such as bialaphos, glufosinate, and the like, 4-HydroxyPhenylPyruvate Dioxygenase (HPPD) inhibitors such as mesotrione, isoxaflutole, and the like, 5-EnolPyruvylShikimate-3-Phosphate Synthase (EPSPS) inhibitors such as glyphosate and the like, and Acetyl-Coenzyme A Carboxylase (ACCase) inhibitors such as haloxyfop, quizalofop, diclofop, and the like. Other examples are known in which transgenically provided proteins provide plant tolerance to herbicide chemical classes such as phenoxy acids herbicides and pyridyloxyacetates auxin herbicides (see WO 2007/053482 A2), or phenoxy acids herbicides and aryloxyphenoxypropionates herbicides (see WO 2005107437 A2, A3). The ability to control multiple pest problems through IR traits is a valuable commercial product concept, and the convenience of this product concept is enhanced if insect control traits and weed control traits are combined in the same plant. Further, improved value may be obtained via single plant combinations of IR traits conferred by a B.t. insecticidal protein such as that of the subject invention with one or more additional HT traits such as those mentioned above, plus one or more additional input traits (e.g. other insect resistance conferred by B.t.-derived or other insecticidal proteins, insect resistance conferred by mechanisms such as RNAi and the like, disease resistance, stress tolerance, improved nitrogen utilization, and the like), or output traits (e.g. high oils content, healthy oil composition, nutritional improvement, and the like). Such combinations may be obtained either through conventional breeding (breeding stack) or jointly as a novel transformation event involving the simultaneous introduction of multiple genes (molecular stack). Benefits include the ability to manage insect pests and improved weed control in a crop plant that provides secondary benefits to the producer and/or the consumer. Thus, the subject invention can be used in combination with other traits to provide a complete agronomic package of improved crop quality with the ability to flexibly and cost effectively control any number of agronomic issues.

All patents, patent applications, provisional applications, and publications referred to or cited herein are incorporated by reference in their entirety to the extent they are not inconsistent with the explicit teachings of this specification.

Unless specifically indicated or implied, the terms "a", "an", and "the" signify "at least one" as used herein.

Following are examples that illustrate procedures for practicing the invention. These examples should not be construed as limiting. All percentages are by weight and all solvent mixture proportions are by volume unless otherwise noted. All temperatures are in degrees Celsius.

Example 1

Construction of Plasmids Encoding DIG-911 and DIG-180, and Expression in Bacterial Hosts DIG-911 protein (Cry1Da2/Cry1Ab chimeric insecticidal toxin; SEQ ID NO:2) consists of a core toxin segment of Cry1Da (amino acids 1 to 594, as disclosed in GENBANK Accession No. 176415.1 and U.S. Pat. No. 5,691,308) and a protoxin segment derived from Cry1Ab (DIG-911 amino acids 595 to 1139), essentially as disclosed in GENBANK Accession No. AFK79795.1). The use of the Cry1Da core toxin segment in combinations with other Cry or Vip insecticidal toxins has been previously disclosed in U.S. Patent Application Publication Nos. 20130007923, 20120331590, 20120331589, and 20120317681, but the use of Cry1Da insecticidal protein to control Corn Earworm (CEW; *Helicoverpa zea* (Boddie)) is not contemplated.

Unless otherwise indicated, molecular biological and biochemical manipulations described in this and subsequent EXAMPLES were performed by standard methodologies as disclosed in, for example, Sambrook et al., eds. (1989 and updates, *Molecular Cloning: A Laboratory Manual,* $2^{nd}$ ed.; Cold Spring Harbor Laboratory Press, Plainview, N.Y.), Ausubel et al., eds. (1995 and updates, *Current Protocols in Molecular Biology*. Greene Publishing and Wiley-Interscience, New York) and Harlow & Lane, eds. (1988, and updates, *Antibodies: A Laboratory Manual*. Cold Spring Harbor Laboratories, Cold Spring Harbor, NY). Standard cloning methods were used in the construction of *Pseudomonas fluorescens* (Pf) expression plasmids engineered to produce DIG-911 and DIG-180 (i.e. Cry1Fa2; SEQ ID NO:4) proteins. Plasmid preparations were performed using the NUCLEOSPIN PLASMID KIT (MACHEREY-NAGEL Inc, Bethlehem, PA), following the low-copy plasmid isolation instructions of the supplier.

The basic cloning strategy entailed subcloning a DNA fragment having the DIG-911 or DIG-180 coding sequence (CDS), as provided by SEQ ID NO:1 and SEQ ID NO:3, respectively, into pDOW1169 at SpeI or XbaI, and XhoI or SalI restriction sites, whereby the DIG-911 and DIG-180 CDS was placed under the expression control of the Ptac promoter and the rrnBT1T2 terminator from plasmid pKK223-3 (PL PHARMACIA, Milwaukee, WI). pDOW1169 is a medium copy plasmid with the RSF1010 origin of replication and a pyrF gene (U.S. Pat. No. 7,618, 799). DNA fragments comprising protein coding region sequences may be cloned into pDOW1169 DNA at a restriction site downstream of a ribosome binding site present within the pDOW1169 sequence, or, alternatively, a separate ribosome binding site may be introduced as a sequence present on the coding region fragment upstream of the protein coding region. DNA of the expression plasmid pDOW2848 (DIG-911) was transformed by electroporation into DC454 cells (a near wild-type *P. fluorescens* strain having mutations ΔpyrF and lsc::lacIQI), and pDAB1817 DNA (DIG-180) was transformed into MB214 cells). Transformed cells were allowed to recover in SOC-Soy hydrolysate medium, and then plated on selective media (M9 glucose agar lacking uracil or on LB medium containing tetracycline at appropriate concentrations; Sambrook et al., supra). Details of the microbiological manipulations for *P. fluorescens* are available in Squires et al. (2004), U.S. Pat. Nos. 7,985,564, 7,681,799, and U.S. patent application No. 20080058262, incorporated herein by reference. Recombinant colonies were identified by restriction digestion of miniprep plasmid DNA.

Growth and expression analysis in shake flasks. Production of DIG-911 and DIG-180 proteins for characterization and insect bioassay was accomplished by shake-flask-grown *P. fluorescens* strain DPf150 (harboring plasmid pDOW2848) or strain Dpf129 (harboring plasmid pDAB1817). Seed cultures grown in M9 medium supplemented with 1% glucose and trace elements were used to inoculate 50 mL of defined minimal medium with 5% glycerol (TEKNOVA Cat. #3D7426, Hollister, CA). Expression of the DIG-911 or DIG-180 genes via the Ptac promoter was induced by addition of isopropyl-B-D-I-thiogalactopyranoside (IPTG) after an initial incubation of 24 hours at 30° with shaking. Cultures were sampled at the time of induction and at various times post-induction. Cell density was measured by optical density at 600 nm ($OD_{600}$). Other culture media suitable for growth of *Pseudomonas fluorescens* may also be utilized, for example, as described in Huang et al. (2007, Prot Cell Fractionation and SDS-PAGE Analysis of Shake Flask Samples. At each sampling time 2 mL aliquots were centrifuged at 14000×g for five minutes, and the cell pellets were stored at −80°. For protein extraction, the pellets were thawed and suspended in 0.5 mL of phosphate buffer pH7.2. Cells were lysed by sonication using a BRANSON 250 SONIFIER (BRANSON ULTRASONICS, Danbury CT) using a ⅛ inch diameter micro tip with a constant output of 20 units. Two 45 second bursts were used with several minutes of cooling the sample on ice between bursts. After the lysate was fractionated by centrifugation in a microfuge for 5 minutes at 14,000 rpm, the supernatant (soluble fraction) was removed and the pellet was suspended in 0.5 ml of phosphate buffer (insoluble fraction).

Samples were mixed 1:3 with 4× Laemmli sample buffer containing [3-mercaptoethanol (Sambrook et al., supra) and boiled for 5 minutes prior to loading onto a NOVEX® 4-20% Tris Glycine SDS polyacrylamide gel (INVITROGEN, Carlsbad, CA). Electrophoresis was performed in Tris Glycine NOVEX® running buffer (INVITROGEN). Gels were stained with BIO-SAFE Coomassie Stain according to the manufacturer's (BIO-RAD Inc., Hercules, CA) protocol.

Inclusion body preparation. Cry protein inclusion body (IB) preparations were performed on cells from *P. fluorescens* fermentations that produced insoluble B.t. insecticidal protein, as demonstrated by SDS-PAGE and MALDI-MS (Matrix Assisted Laser Desorption/Ionization Mass Spectrometry). *P. fluorescens* fermentation pellets were thawed in a 37° water bath. The cells were resuspended to 25% w/v in lysis buffer (50 mM Tris, pH 7.5, 200 mM NaCl, 20 mM EDTA disodium salt (Ethylenediaminetetraacetic acid), 1% Triton X-100, and 5 mM Dithiothreitol (DTT); 5 mL/L of bacterial protease inhibitor cocktail (P8465 SIGMA-ALDRICH, St. Louis, MO) were added just prior to use. Thorough suspension was obtained using a hand-held homogenizer at lowest setting (TISSUE TEAROR™, BIOSPEC PRODUCTS, Inc., Bartlesville, OK). Lysozyme (25 mg of SIGMA L7651, from chicken egg white) was added to the cell suspension by mixing with a metal spatula, and the suspension was incubated at room temperature for one hour. The suspension was cooled on ice for 15 minutes, then sonicated using a BRANSON 250 SONIFIER (two 1-minute sessions, at 50% duty cycle, 30% output). Cell lysis was checked by microscopy. An additional 25 mg of lysozyme were added if necessary, and the incubation and sonication were repeated. When cell lysis was confirmed via microscopy, the lysate was centrifuged at 11,500×g for 25 minutes (4°) to form the IB pellet, and the supernatant was discarded. The IB pellet was resuspended with 100 mL lysis buffer, homogenized with the hand-held mixer and centrifuged as above. The IB pellet was repeatedly washed by resuspension (in 50 mL lysis buffer), homogenization, sonication, and centrifugation until the supernatant became colorless and the IB pellet became firm and off-white in color. For the final wash, the IB pellet was resuspended in sterile-filtered (0.22 μm) distilled water containing 2 mM EDTA, and centrifuged. The final pellet was resuspended in sterile-filtered distilled water containing 2 mM EDTA, and stored in 1 mL aliquots at −80°. SDS-PAGE analysis and quantitation of protein in IB preparations were done by thawing a 1 mL aliquot of IB pellet and diluting 1:20 with sterile-filtered distilled water. The diluted sample was then boiled with 4× reducing sample buffer (250 mM Tris, pH6.8, 40% glycerol (v/v), 0.4% Bromophenol Blue (w/v), 8% SDS (w/v) and 8% B-Mercapto-ethanol (v/v)) and loaded onto a NOVEX® 4-20% Tris-Glycine, 12+2 well gel (INVITROGEN) run with 1× Tris/Glycine/SDS buffer (BIO-RAD). The gel was run for approximately 60 min at 200 volts then stained with Coomassie Blue (50% G-250/50% R-250 in 45% methanol, 10% acetic acid), and destained with 7% acetic acid, 5% methanol in distilled water. Quantification of target bands was done by comparing densitometric values for the bands against Bovine Serum Albumin (BSA) samples run on the same gel to generate a standard curve.

Solubilization of Inclusion Bodies. Six mL of inclusion body suspensions from Pf isolates DPf150 or Dpf129 (containing about 30 mg/mL of DIG-911 or DIG-180 protein) were centrifuged on the highest setting of a microfuge (approximately 14,000×g) to pellet the inclusions. The storage buffer supernatant was removed and replaced with 25 mL of 100 mM sodium carbonate buffer, pH11, in a 50 mL conical tube. Inclusions were resuspended using a pipette and vortexed to mix thoroughly. The tube was placed on a gently rocking platform at 4° overnight to extract the target protein. The extract was centrifuged at 30,000×g for 30 min at 4°, and the resulting supernatant was concentrated 5-fold using an AMICON ULTRA-15 regenerated cellulose centrifugal filter device (30,000 Molecular Weight Cutoff; MILLIPORE). The sample buffer was then changed to 10 mM CAPS (3-(cyclohexamino)-1-propanesulfonic acid) pH10, using disposable PD-10 columns (GE HEALTHCARE, Piscataway, NJ).

SDS-PAGE analysis and quantitation of protein in IB preparations were done by thawing a 1 mL aliquot of IB pellet and diluting 1:20 with sterile-filtered distilled water. The diluted sample was then boiled with 4× reducing sample buffer (250 mM Tris, pH6.8, 40% glycerol (v/v), 0.4% Bromophenol Blue (w/v), 8% SDS (w/v) and 8% B-Mercapto-ethanol (v/v)) and loaded onto a NOVEX® 4-20% Tris-Glycine, 12+2 well gel (INVITROGEN) run with 1× Tris/Glycine/SDS buffer (BIO-RAD). The gel was run for approximately 60 min at 200 volts then stained with Coomassie Blue (50% G-250/50% R-250 in 45% methanol, 10% acetic acid), and destained with 7% acetic acid, 5% methanol in distilled water. Quantification of target bands was done by comparing densitometric values for the bands against Bovine Serum Albumin (BSA) samples run on the same gel to generate a standard curve. The concentrated extract was prepared for electrophoresis by diluting 1:50 in NuPAGE® LDS sample buffer (INVITROGEN) containing 5 mM dithiothreitol as a reducing agent and heated at 95° for 4 minutes. The sample was loaded in duplicate lanes of a 4-12% NuPAGE® gel alongside five BSA standards ranging from 0.2 to 2 ug/lane (for standard curve generation). Voltage was applied at 200V using MOPS SDS running buffer (INVITROGEN) until the tracking dye reached the bottom of the gel. The gel was stained with 0.2% Coomassie Blue G-250 in 45% methanol, 10% acetic acid, and destained, first briefly with 45% methanol, 10% acetic acid, and then at length with 7% acetic acid, 5% methanol until the background cleared. Following destaining, the gel was scanned with a BIO-RAD FLUOR-S MULTIIMAGER. The instrument's QUANTITY ONE v.4.5.2 Software was used to obtain background-subtracted volumes of the stained protein bands and to generate the BSA standard curve that was used to calculate the concentration of DIG-911 or DIG-180 protein in the stock solution.

Example 2

Activity of DIG-911 and DIG-180 Insecticidal Toxins Produced in *Pseudomonas fluorescens* Against CEW Larvae Sample preparation and bioassays. Inclusion body preparations in 10 mM CAPS pH 10 were diluted in the same buffer to deliver a dose of 3,000, 1,000, 333.3, 111.1, 37.0, 12.3 or 4.1 ng/cm$^2$ of the target Cry1Da protein. All bioassays contained control treatments consisting of 10 mM CAPS pH 10 buffer or water, which served as background checks for mortality or growth inhibition.

Protein concentrations in bioassay buffer were estimated by gel electrophoresis using BSA to create a standard curve for gel densitometry, which was measured using a BIORAD imaging system (FLUOR-S MULTIIMAGER with QUANTITY ONE software version 4.5.2). Proteins in the gel matrix were stained with Coomassie Blue-based stain and destained before reading.

Larvae of CEW were hatched from eggs obtained from a colony maintained by a commercial insectary (BENZON RESEARCH INC., Carlisle, PA). The bioassays were conducted in 128-well plastic trays specifically designed for insect bioassays (C-D INTERNATIONAL, Pitman, NJ). Each well contained 1.5 mL of Multi-species Lepidoptera diet (SOUTHLAND PRODUCTS, Lake Village, AR). A 40 μL aliquot of protein sample was delivered by pipette onto the 1.5 cm$^2$ diet surface of each well (26.7 μL/cm$^2$). Diet concentrations were calculated as the amount (ng) of insecticidal toxin protein per square centimeter (cm$^2$) of surface area in the well. The treated trays were held in a fume hood until the liquid on the diet surface had evaporated or was absorbed into the diet.

Within 24 to 48 hours of eclosion, individual larvae were picked up with a moistened camel hair brush and deposited on the treated diet, one larva per well. The infested wells were then sealed with adhesive sheets of clear plastic, vented to allow gas exchange (C-D INTERNATIONAL). Bioassay trays were held under controlled environmental conditions (28°, ~60% Relative Humidity, 16:8 (Light: Dark)) for 5 days, after which time the total number of insects exposed to each protein sample, the number of live and dead insects, and the weight of surviving insects were recorded. Percent mortality and percent growth inhibition were calculated for each treatment. Growth inhibition (GI) was calculated as follows:

$$GI=[1-(TWIT/TNIT)/(TWIBC/TNIBC)]$$

where TWIT is the Total Weight of Insects in the Treatment,

TNIT is the Total Number of Insects in the Treatment

TWIBC is the Total Weight of Insects in the Background Check (Buffer control), and TNIBC is the Total Number of Insects in the Background Check (Buffer control).

The mortality and growth inhibition data were analyzed by a nominal logistic regression (P<0.05). The GI50 was determined to be the concentration of insecticidal toxin protein in the diet at which the GI value was 50%, and the LC50 (50% Lethal Concentration) was recorded as the concentration of insecticidal toxin protein in the diet at which 50% of test insects were killed. Statistical analysis (One-way ANOVA) was done using JMP® Pro software (version 9.0.3; SAS, Cary, NC). Table 1 shows the activities of DIG-911 and DIG-180 proteins as measured in diet bioassays

TABLE 1

Activities of DIG-911 And Cry1Fa proteins in diet bioassays against neonate larvae of corn earworm (CEW).

| | | Mortality | | Growth Inhibition | |
|---|---|---|---|---|---|
| Insect | Protein | $LC_{50}$ (ng/cm$^2$) | 95% CI* | $GI_{50}$ (ng/cm$^2$) | 95% CI |
| CEW | DIG-911 | 2193 | (1551-3351) | 75 | (49-116) |
| | Cry1Fa2 | 10771 | (6158-23007) | 94 | (45-195) |

*= Confidence Interval

The data of Table 1 document the surprising discovery that the DIG-911 protein, comprising the Cry1Da core toxin segment, exhibits both mortality and growth inhibition activity against corn earworm (CEW) larvae. This result is in contrast to results reported by others that the Cry1Da protein is inactive against corn earworm (See Karim et al. (2000) Pesticide Biochemistry and Physiology 67 (3): 198-216; and Frankenhuyzen (2009) Journal of Invertebrate Pathology. 101:1-16).

Example 3

Construction of Plant Transformation Vectors

Gateway® (INVITROGEN) entry vectors were constructed by standard molecular cloning methods. Entry vector pDAB 109825 comprises a maize-optimized coding sequence (SEQ ID NO:5) that encodes a Cry1Da2 core toxin insecticidal protein (SEQ ID NO:6). Entry vector pDAB 109840 comprises a maize-optimized coding sequence that encodes a Cry1Da2 full length insecticidal protein. Plant expression of the Cry1Da2 core toxin coding sequence is under the control of a copy of a maize ubiquitin 1 promoter with associated intron 1 (U.S. Pat. No. 5,510,474). A fragment comprising a 3'UTR from a maize peroxidase 5 gene (ZmPer5 3'UTR; U.S. Pat. No. 6,699,984) was used to terminate transcription of the Cry1Da2 mRNA. A transformation/expression vector (pDAB109841) for *Agrobacterium*-mediated maize embryo transformation was constructed through the use of standard cloning methods and Gateway® recombination reactions employing a typical destination binary vector (pDAB 109805) and entry vector pDAB 109825 described above. Binary destination vector pDAB 109805 comprises an AAD-1 herbicide tolerance protein coding region (U.S. Pat. No. 7,838,733, and Wright et al. (2010) Proc. Natl. Acad. Sci. U.S.A. 107:20240-20245) under the expression control of a copy of a sugarcane bacilliform virus promoter (SCBV; essentially as described in U.S. Pat. No. 6,093,569). A synthetic 5'UTR sequence comprised of sequences from a Maize Streak Virus (MSV) coat protein gene 5'UTR and intron 6 from a maize Alcohol Dehydrogenase 1 (ADH1) gene is positioned between the 3' end of the SCBV promoter segment and the start codon of the AAD-1 coding region. A fragment comprising a 3'UTR from a maize lipase gene (as above) was used to terminate transcription of the AAD-1 mRNA.

A negative control binary vector (pDAB101556) comprised a yellow fluorescent protein (YFP) marker gene coding region (Shagin et al. (2004) Molecular Biology and Evolution 21:841-850) under the expression control of a copy of a maize ubiquitin 1 promoter with intron1 (as above) and a fragment comprising a 3'UTR from a maize peroxidase 5 gene (ZmPer5 3'UTR; U.S. Pat. No. 6,699,984). pDAB101556 further comprises an AAD-1 herbicide tolerance protein coding region (as above) under the expression control of a second copy of a maize ubiquitin 1 promoter with intron1 (as above), and a 3'UTR from a maize lipase gene (as above).

Example 4

*Agrobacterium*-Mediated Maize Transformation

*Agrobacterium*-mediated transformation was used to stably integrate a Cry1Da2 core toxin coding region into the plant genome and thus generate transgenic maize cells, tissues, and plants that produce a full length or truncated Cry1Da2 insecticidal protein. Maize transformation methods employing superbinary or binary transformation vectors are known in the art, as described, for example, in International PCT Publication No. WO2010/120452. Transformed tissues were selected by their ability to grow on R-Haloxyfop-containing medium.

*Agrobacterium* Culture Initiation Glycerol stocks of the project vectors were provided in the *Agrobacterium tumefaciens* host strain DAt13192 (WO 2012/016222A2). *Agrobacterium* cultures were streaked from glycerol stocks onto AB minimal medium (Watson, et al., (1975) J. Bacteriology 123:255-264) and incubated at 20° C. in the dark for 3 days containing appropriate antibiotics. The cultures were then streaked onto a plate of YEP medium (gm/L: yeast extract, 10; Peptone, 10; NaCl, 5) with antibiotics and incubated at 20° C. in the dark for 1-3 day.

On the day of an experiment, a mixture of Inoculation Medium and acetosyringone (Frame et al. (2011) Methods in Molecular Biology 710:327-341) was prepared in a volume appropriate to the number of constructs in the experiment and pipetted into a sterile, disposable, 250 mL flask. Inoculation Medium contains: 2.2 gm/L MS salts; Modified MS Vitamins (Frame et al., ibid.) 68.4 gm/L sucrose; 36 gm/L glucose; 115 mg/L L-proline; and 100 mg/L myo-inositol; at pH 5.4.) Acetosyringone was added to the flask containing Inoculation Medium to a final concentration of 200 uM from a 1 M stock solution in 100% dimethyl sulfoxide.

For each construct, 1 inoculating loopful of *Agrobacterium* from the YEP plate was suspended in 15 mL of the Inoculation Medium/acetosyringone mixture inside a sterile, disposable, 50 mL centrifuge tube, and the optical density of the solution at 550 nm ($OD_{550}$) was measured in a spectrophotometer. The suspension was then diluted to $OD_{550}$ of 0.3 to 0.4 using additional Inoculation Medium/acetosyringone mixture. The tube of *Agrobacterium* suspension was then placed horizontally on a platform shaker set at about 75 rpm at room temperature and shaken for 1 to 4 hours before use.

Ear sterilization and embryo isolation. Ears from *Zea mays* inbred line B104 (Hallauer, et al. (1997) Crop Science 37:1405-1406) were produced in a greenhouse and harvested 10 to 12 days post pollination. Harvested ears were de-husked and surface-sterilized by immersion in a 20% solution of commercial bleach (Ultra Clorox® Germicidal Bleach, 6.15% sodium hypochlorite; with two drops of TWEEN 20) for 20 minutes, followed by three rinses in sterile, deionized water inside a laminar flow hood. Immature zygotic embryos (1.8 to 2.2 mm long) were aseptically excised from each ear and distributed into one or more micro-centrifuge tubes containing 2.0 mL of *Agrobacterium* suspension into which 2 μL of 10% BREAK-THRU® S233 surfactant (EVONIK INDUSTRIES; Essen, Germany) had been added.

*Agrobacterium* co-cultivation. Following isolation, the embryos were placed on a rocker platform for 5 minutes. The contents of the tube were then poured onto a plate of Co-cultivation Medium, which contains 4.33 gm/L MS salts; Modified MS Vitamins; 30 gm/L sucrose; 700 mg/L L-proline; 3.3 mg/L Dicamba in KOH (3,6-dichloro-o-anisic acid or 3,6-dichloro-2-methoxybenzoic acid); 100 mg/L myo-inositol; 100 mg/L Casein Enzymatic Hydrolysate; 15 mg/L $AgNO_3$; 200 μM acetosyringone in DMSO; and 3 gm/L agar (SIGMA-ALDRICH, plant cell culture tested) at pH 5.8. The liquid *Agrobacterium* suspension was removed with a sterile, disposable, transfer pipette and co-cultivation plate containing the embryos was placed at the back of the laminar flow hood with the lid ajar for 30 minutes, after which time the embryos were oriented with the scutellum facing up using sterile forceps with the aid of a microscope. The plate was returned to the back of the laminar flow hood with the lid ajar for a further 15 min. The plate was then closed, sealed with 3M™ Micropore™ medical tape, and placed in an incubator at 25° C. with continuous light at approximately 60 $\mu Em^{-2}$ $sec^{-1}$ light intensity Callus Selection and Regeneration of Transgenic Events. Following the co-cultivation period, embryos were transferred to Resting Medium, which is composed of 4.33 gm/L MS salts; Modified MS Vitamins; 30 gm/L sucrose; 700 mg/L L-proline; 3.3 mg/L Dicamba in KOH; 100 mg/L myo-inositol; 100 mg/L Casein Enzymatic Hydrolysate; 15 mg/L $AgNO_3$; 0.5 gm/L MES (2-(N-morpholino) ethanesulfonic acid monohydrate; Phytotechnologies labr.; Lenexa, KS); 250 mg/L Cefotaxime; and 7.0 gm/L agar; at pH 5.8. No more than 36 embryos were moved to each plate. The plates were wrapped with Micropore™ tape and incubated at 27° C. with continuous light at approximately 50 $\mu Em^{-2}$ $sec^{-1}$ light intensity for 7 to 10 days. Embryos with callus (<18/plate) were then transferred onto Selection Medium I, which is comprised of Resting Medium (above) but with only 6.5 gm/L agar, and with 100 nM R-Haloxyfop acid (0.0362 mg/L. The plates were wrapped with Micropore™ tape and incubated at 27° C. with continuous light at approximately 50 $\mu Em^{-2}$ $sec^{-1}$ light intensity for 7 days. Proliferated Callus (<12/plate) were then transferred to Selection Medium II, which is comprised of Resting Medium (above) but with only 6.5 gm/L agar, and with 500 nM R-Haloxyfop acid (0.181 mg/L). The plates were wrapped and incubated at 27° C. with continuous light at approximately 50 $\mu Em^{-2}$ $sec^{-1}$ light intensity for 14 days.

At this stage, resistant calli (<9/plate) were moved to Pre-Regeneration medium. Pre-Regeneration Medium contains 4.33 gm/L MS salts; Modified MS Vitamins; 45 gm/L sucrose; 350 mg/L L-proline; 100 mg/L myo-inositol; 50 mg/L Casein Enzymatic Hydrolysate; 1.0 mg/L $AgNO_3$; 0.5 gm/L MES; 0.5 mg/L naphthaleneacetic acid in NaOH; 2.5 mg/L abscisic acid in ethanol; 1 mg/L 6-benzylaminopurine; 250 mg/L Cefotaxime; 5.5 gm/L agar; and 500 nM R-Haloxyfop acid (0.181 mg/L), at pH 5.8. The plates were wrapped and incubated at 27° C. with continuous light at approximately 50 $\mu Em^{-2}$ $sec^{-1}$ light intensity for 7 days. Regenerating calli (<6/plate) were then transferred to Regeneration Medium in Phytatrays™ (Sigma-Aldrich) and incubated at 28° C. with 16 hours light/8 hours dark per day at approximately 150 μmol $m^{-2}$ $s^{-1}$ light intensity for 14 days or until shoots developed. Regeneration Medium contains 4.33 gm/L MS salts; Modified MS Vitamins; 60 gm/L sucrose; 0.50 gm/L MES; 125 mg/L Cefotaxime; 5.5 gm/L agar; and 500 nM R-Haloxyfop acid (0.181 mg/L), at pH 5.8. Small shoots with primary roots were then isolated and transferred to Elongation Medium without selection (i.e. Regeneration Medium without R-Haloxyfop acid and with 30 gm/L sucrose instead of 60 gm/L sucrose) for further growth. Rooted plantlets about 6 cm or taller were transplanted into soil and moved to a growth chamber for hardening off.

Transfer and establishment of $T_0$ plants in the greenhouse for assay and seed production. Transformed plant tissues selected by their ability to grow on medium containing Haloxyfop were transplanted from Phytatrays™ to small pots (T. O. Plastics, 3.5" SVD) filled with growing media (PROMIX BX; Premier Tech Horticulture), covered with humidomes (Arco Plastics Ltd.), and then hardened-off in a growth room (28° C. day/24° C. night, 16-hour photoperiod, 50-70% RH, 200 $\mu Em^{-2}$ $sec^{-1}$ light intensity). When plants reached the V3-V4 stage, they were transplanted into Sunshine Custom Blend 160 soil mixture and grown to flowering in the greenhouse (Light Exposure Type: Photo or Assimilation; High Light Limit: 1200 PAR; 16-hour day length; 27° C. day/24° C. night). Putative transgenic plantlets were analyzed for transgene copy number by quantitative real-time PCR assays using primers designed to detect relative copy numbers of the transgenes, and events having only one or two copies of the integrated Cry1Da2 gene were transplanted into 5 gallon pots. Observations were taken periodically to track any abnormal phenotypes. Plants of the $T_1$ generation were obtained by self-pollinating the silks of $T_0$ transgenic plants with pollen collected from the $T_0$ plants and planting the resultant seeds. $T_1$ seeds from event 109841 [3]-106 were planted and selected by spraying the plants with Quizalofop, and keeping the surviving plants until the reproduction stage to obtain silks for corn earworm bioassays and western blot analyses.

Transgenic maize plants were similarly produced following transformation with binary vector pDAB 101556 harboring a yellow fluorescent protein gene expression cassette.

Example 5

Molecular and Biochemical Analyses of Transgenic Maize Tissues

Hydrolysis Probe qPCR for copy number analysis. Molecular analyses were employed to screen for low copy, simple events. Leaf tissue was collected from rooted putative transgenic plants before transplanting to soil. DNA was extracted with a QIAGEN MagAttract™ kit using the Biosprint96, QIAGEN extraction robot and the supplier's recommended protocols. Integrated transgene copy number analysis was performed using specific Hydrolysis Probe assays for the AAD-1 gene. In addition, contamination by inadvertent integration of the binary vector plasmid backbone was detected by a Hydrolysis Probe assay specific for the Spectinomycin (Spec) resistance gene borne on the binary vector backbone. Hydrolysis Probe assay for endogenous maize genes Invertase; (GenBank™ Accession No. U16123) was developed as internal reference standard. Table 2 lists the oligonucleotide sequences of the Hydrolysis Probe assay components (synthesized by Integrated DNA Technologies, Coralville, IA & Applied Biosystems, Foster City, CA). Biplex Hydrolysis Probe PCR reactions were set up according to Table 3 with about 10 ng of DNA, and assay conditions are presented in Table 4.

TABLE 2

List of forward and reverse nucleotide primers and fluorescent probes used for transgene copy number and relative expression detection.

| Gene Detected | Oligo-nucleo-tide ID* | SEQ ID NO: | Sequence |
|---|---|---|---|
| AAD-1 | AADIF | 7 | TGTTCGGTTCCCTCT ACCAA |
| | AAD1R | 8 | CAACATCCATCA CCTTGACTGA |
| | AAD1P *(FAM Probe) | 9 | CACAGAACCGTCGCT TCAGCAACA |
| Spec | SPC1A | 10 | CTTAGCTGGATA ACGCCAC |
| | SPC1S | 11 | GACCGTAAGGCT TGATGAA |
| | TQSPC (FAM Probe) | 12 | CGAGATTCTCCGC GCTGTAGA |
| Maize | InvertaseF | 13 | TGGCGGACGACGA CTTGT |
| Invertase | InvertaseR | 14 | AAAGTTTGGAGGC TGCCGT |
| | InvertaseP (HEX Probe) | 15 | CGAGCAGACCGCC GTGTACTT |

*Fluorescent probe labels are: FAM = 6-Carboxy Fluorescein Amidite; HEX = hexachloro-fluorescein; MGB & VIC = "Minor Groove Binder"; VIC® is a proprietary fluorescent label from INVITROGEN.

TABLE 3

Hydrolysis Probe PCR mixture for transgene DNA copy number analysis.

| Reaction Component | μL | Final Concentration |
|---|---|---|
| Water | 0.6 | |
| ROCHE 2X Master Mix | 5 | 1X |
| Transgene Forward Primer (10 μM) | 0.4 | 0.4 μM |
| Transgene Reverse Primer (10 μM) | 0.4 | 0.4 μM |
| Transgene Probe (5 μM) | 0.4 | 0.2 μM |
| Invertase Forward Primer (10 μM) | 0.4 | 0.4 μM |
| Invertase Reverse Primer (10 μM) | 0.4 | 0.4 μM |
| Invertase Probe (5 μM) | 0.4 | 0.2 μM |

TABLE 4

Thermocycler conditions for Hydrolysis Probe PCR amplification

| PCR Steps | Temp (° C.) | Time | No. of cycles |
|---|---|---|---|
| Denature/Activation | 95 | 10 min | 1 |
| Denature | 95 | 10 sec | 40 |
| Anneal/Extend | 60 | 40 sec | |
| Acquire | 72 | 1 sec | |
| Cool | 40 | 10 sec | 1 |

For amplification, LIGHTCYCLER®480 Probes Master mix (Roche Applied Science, Indianapolis, IN) was prepared at 1× final concentration in a 10 μL volume multiplex reaction, 0.4 uM of each primer, and 0.2 uM of each probe. The FAM (6-Carboxy Fluorescein Amidite) fluorescent moiety was excited at 465 nm and fluorescence was measured at 510 nm; the corresponding value for the HEX (hexachloro-fluorescein) fluorescent moiety were 533 nm and 580 nm. The level of fluorescence generated for each reaction was analyzed using the Roche Lightcycler®480 Real-Time PCR system according to the manufacturer's recommendations. Transgene copy number was determined by comparison of Lightcycler®480 outputs of Target/Reference gene values for unknown samples to Target/Reference gene values of known copy number standards (1-Copy representing hemi-zygous plants, 2-Copy representing homozygous plants).

Cp scores, i.e., the point at which the florescence signal crosses the background threshold using the fit points algorithm (Lightcycler® software release 1.5), and the Relative Quant module, were used to perform the analysis of real time PCR data.

In the Lightcycler® Fit Points Algorithm software, a graph of the data is made by plotting the logarithm of the input DNA template concentration against the measured Cp values. The slope of the curve is a desired comparison parameter; therefore the initial log input number can be an arbitrary starting point on the curve, with the caveat that the arbitrary concentration values used for input DNA template are representative of the actual serial dilution used. For example, for a 10-fold serial dilution series, the actual inputs concentrations may be 1000, 100, 10 etc., for which points the LC480 Fit Points Algorithm software plots 3, 2, 1 etc. as the logarithms of the inputs. Using a linear regression, the resulting best fit of this line (input log vs Cp) is then used to estimate a slope (m) from an equation of the form y=mx+b. There is an inverse relationship between the starting template amount and Cp value, and therefore the slope (m) is always negative.

A perfect (i.e. 100% efficient) PCR reaction doubles the total template every cycle. PCR efficiency (Eff) is calculated as: Eff=10e(−l/m). Thus, the slope (m) of the graph of log input vs Cp will be −3.3219 for a perfectly efficient reaction (whose efficiency is defined as 2.00).

In other words, a 100% efficient PCR reaction is defined by: 2.0=10e(−1/−3.3219) The LC480 Fit Points Algorithm software reports the efficiency value by the first formula. So a 99% efficient reaction has an Eff value of 1.99 rather than 0.99. To express this as a percent efficiency, subtract 1 from this value and multiply by 100. Or, % Eff=[(10e(−l/m)−1)]×100

Detection of plant-produced truncated Cry1Da2 protein. Proteins were extracted from 200 to 240 mg of ear silks (collected from unpollinated ears) in 0.6 mL of PBST (PBS buffer containing 0.05% Tween 20). A 2 mm steel bead was added, the tubes were capped and secured in a GENO/GRINDER (CERTIPREP; Metuchen, NJ), and shaken for 5 min at 1500 rpm. Tubes were centrifuged at 4000 rpm for 7 min at 4° C., and supernatants containing the soluble proteins were stored at −80° C. until used.

Total protein concentrations were determined using a PIERCE 660 nm PROTEIN ASSAY kit (THERMO SCIENTIFIC; Rockford, IL) following the supplier's instructions. Protein immunoblot analyses were conducted using a polyclonal antibody generated in rabbits using standard procedures (See, for example, Harlow, E., and Lane, D. P. (1988) Antibodies: A Laboratory Manual. Cold Springs Harbor Laboratories, Cold Spring Harbor, NY, and updates thereof). Samples were prepared and proteins were separated by electrophoresis through NUPAGE 4-12% Bis-Tris gels in MES running buffer according to the manufacturer's suggested protocol for denaturing electrophoresis (INVITROGEN). Proteins were transferred onto nitrocellulose membrane for 80 min, at 30 V in NUPAGE transfer buffer. Blots were blocked for 1 hour at room temperature in 5% milk/PBST (PBS with 0.05% Tween-20) and then probed with primary antibody (specific for Cry1Da core toxin protein) and then secondary antibodies for one hour each at room temperature in blocking solution, with rinsing in between each antibody for 15 minutes in PBST. Development of blots was done using PIERCE's ECL WESTERN blotting substrate according the manufacturer's protocol (THERMO FISHER SCIENTIFIC, Rockford, IL). The presence of truncated Cry1Da proteins was confirmed in extracts from duplicate samples of the silk tissues of maize plants generated from event 109841 [3]-106 (plants 109841 [3]-106.AJ001.008, 109841 [3]-106.AJ001.013, 109841 [3]-106.AJ001.020, 109841 [3]-106.AJ001.027, and 109841 [3]-106.AJ001.028). Two bands were typically detected, one at mobility corresponding to approximately 65 kDa, which corresponds to the molecular size of the Cry1Da2 protein encoded by construct pDAB109841, and a second band having a mobility corresponding to proteins somewhat smaller than 65 kDa. The smaller proteins may correspond to the products remaining after cleavage of amino acids 1-28 from the N-terminus of the Cry1Da core toxin protein. (Processing of a few N-terminal amino acids from Cry1 proteins is often detected.) No such bands were seen in silk extracts from non-transgenic B104 plants.

simple percent leaf area damage score was taken for each leaf piece. Damage scores for each test were averaged.

Corn earworm silk bioassays. Unpollinated ears were collected, their length was measured, and the ears were stored at 4° C. until used for bioassay. About 10 mL of 2% water agar was placed in the bottom each assay well (about 1 inch square) of a 32-well-bioassay tray to supply moisture to the silks and corn earworm larvae. Five strands of silks (about 10 cm long) were fed to two CEW neonates in each well. Each event was tested in four replicates (wells) in a completely randomized format. After insect infestation, trays were sealed with perforated sticky lids to allow ventilation during the test. Trays were placed at 28° C., 60% RH, 16 hours light: 8 hours dark. At 3 days after infestation, the percent silk damage was recorded by visual assessment of the amount of feces on the silk tissues. The numbers of alive, dead and missing insects were recorded per event and percent larval mortality was estimated.

Plant-produced Cry1Da activity on CEW larvae. Immunoblot analyses detected Cry1Da core toxin protein in silks of ears of T1 pDAB109841 transgenic plants, and the silks provided excellent protection against feeding damage by *H. zea* larvae, having only 4.6% silk damage in the bioassays (Table 6). Silks from negative control transgenic maize plants producing the non-insecticidal yellow fluorescent

TABLE 5

Analysis of T1 plants for RNA relative transcript level (RTL) and protein expression.

| | | | | RNA | | | Protein | | | |
|---|---|---|---|---|---|---|---|---|---|---|
| Background | Description | Total number of events | Events | total RNA RTL | Total plants | Average RTL/event | Western | Total expression fmole/cm$^2$ | Total plants | Average expression fmole/cm$^2$ |
| | | | 109840[1]-254.AJ001 | 3.7 | 5 | 0.7 | positive | 820 | 5 | 164.0 |
| | | | 109840[2] -121.AJ001 | 2.3 | 5 | 0.5 | negative | 356 | 4 | 89.0 |
| 109840 | Cry1Da FL | 2 | background summary | 5.9 | 10 | 0.6 | | 1176.0 | 9.0 | 130.7 |
| | | | 109841 [1]-183.AJ001 | 2.73 | 5 | 0.5 | positive | 2270 | 5 | 454.0 |
| | | | 109841 [1]-185. AJ001 | 1.99 | 5 | 0.4 | positive | 3220 | 5 | 644.0 |
| | | | 109841 [1]-187.AJ001 | 1.71 | 5 | 0.3 | positive | 2800 | 5 | 560.0 |
| | | | 109841 [1]-188. AJ001 | 1.86 | 5 | 0.4 | negative | 3350 | 5 | 670.0 |
| | | | 109841 [1]-189.AJ 001 | 2.28 | 5 | 0.5 | | 4000 | 5 | 800.0 |
| | | | 109841 [2]-021. AJ001 | 2.35 | 5 | 0.5 | negative | 2990 | 5 | 598.0 |
| | | | 109841 [3]-106.AJ001 | 1.82 | 5 | 0.4 | | 3670 | 5 | 734.0 |
| | | | 109841 [3]-108.AJ001 | 2.62 | 5 | 0.5 | | 4750 | 5 | 950.0 |
| | | | 109841 [3]-116. AJ001 | 3.16 | 5 | 0.6 | positive | 3910 | 5 | 782.0 |
| 109841 | Cry1Da Tr | 9 | background summary | 20.52 | 45 | 0.5 | | 30960.00 | 45.00 | 688.0 |

* Measurements were conducted by Western analysis and quantified by LC/MS/MS as known in the art.

Example 6

Bioassay of Transgenic Maize Tissues

V5 Leaf Bioassays with $T_1$ Maize Events. Bioassay trays (32-wells/tray; C-D International) were partially filled with a 2% agar solution and the agar was allowed to solidify. Two leaf sections (about one square inch in area) were taken from each plant and each was placed in a separate well of the 32-well trays. Ten neonate *Helicoverpa zea* (CEW) larvae (about 24 to 48 hr after eclosion) were placed into each well. The trays were sealed with perforated sticky lids to allow ventilation during the test and were then placed at 28° C., 40% RH, 16 hours light: 8 hours dark. After three days, a protein (YFP; construct pDAB 101556), or non-transgenic B104 plants, experienced 90% to 95% mean silk damage by *H. zea* larvae. In addition, the mortality of larvae feeding on silk from plants producing the Cry1Da core toxin protein was 26.8%, while no mortality of the larvae was observed on the negative control plant samples. The Cry1Da construct gave excellent leaf protection of the V5 stage samples, with the pDAB109851 transgenic plants having 12% to 25% leaf damage caused by *H. zea* (Table 6), whereas the negative control plants (B104 and YFP-producing) experienced almost 100% leaf damage. The results from both silk and leaf bioassays demonstrated that the Cry1Da core toxin protein is highly effective in protecting maize plants from damage from *H. zea* larvae.

TABLE 6

Results of bioassays with *H. zea* neonate larvae on samples from Cry1Da core toxin-producing plants, as compared to negative control plants. Means within a column were separated by the Tukey-Kramer HSD test.

| Plant ID | Cry1Da Protein immunoblot | Ear Length (cm) | % CEW Mortality* | Mean % Silk Damage* | Mean Leaf Damage at V5 |
|---|---|---|---|---|---|
| pDAB109841 Events | | | | | |
| 109841[3]-106.AJ001.008 | + | 11.4 | 0.0 | 5.0 | 25 |
| 109841[3]-106.AJ001.008 | + | 14.2 | 28.6 | 7.5 | |
| 109841[3]-106.AJ001.013 | + | 13.6 | 0.0 | 5.0 | 16.7 |
| 109841[3]-106.AJ001.013 | + | 14 | 12.5 | 3.8 | |
| 109841[3]-106.AJ001.020 | + | 11.9 | 50.0 | 2.5 | 20 |
| 109841[3]-106.AJ001.020 | + | 16.3 | 50.0 | 5.0 | |
| 109841[3]-106.AJ001.027 | + | 12.5 | 75.0 | 3.8 | 20 |
| 109841[3]-106.AJ001.027 | + | 13.2 | 37.5 | 3.8 | |
| 109841[3]-106.AJ001.028 | + | 13.9 | 14.3 | 5.0 | 11.7 |
| 109841[3]-106.AJ001.028 | + | 11.2 | 0.0 | 5.0 | |
| Overall Averages | NA** | 13.2 | 26.8 (A)*** | 4.6(B)*** | 18.7(B)*** |
| Transgenic Negative Controls: pDAB101556 Events | | | | | |
| 101556[3]-004.001AJ.002 | – | 9.9 | 0.0 | 86.3 | 95-100 |
| 101556[3]-004.001AJ.002 | – | 18.5 | 0.0 | 83.8 | |
| 101556[3]-004.001AJ.002 | – | 13.9 | 0.0 | 95.0 | |
| 101556[3]-004.001AJ.007 | – | 15 | 0.0 | 95.0 | |
| 101556[3]-004.001AJ.008 | – | 12.7 | 0.0 | 93.8 | |
| Overall Averages | NA | 14.2 | 0.0 (B) | 90.8 (A) | 95-100 (A) |
| Non-transgenic Negative Controls: B104 Plants | | | | | |
| B104 #46749 | – | 9 | 0.0 | 88.3 | 95-100 |
| B104 #47153 | – | 9.4 | 0.0 | 97.5 | |
| B104 #47153 | – | 12.2 | 0.0 | 96.3 | |
| B104 #47156 | – | 13.7 | 0.0 | 95.0 | |
| B104 #47157 | – | 14.1 | 0.0 | 91.7 | |
| B104 #47869 | – | 12.6 | 0.0 | 97.5 | |
| B104 #47870 | – | 11.4 | 0.0 | 98.8 | |
| Overall Averages | NA | 11.8 | 0.0 (B) | 95.0 (A) | 95-100 (A) |

*Average of 4 replicates

**NA = Not Applicable

***Levels not connected by same letter within a column are significantly different.

Table 7 shows percent mortality, percent leaf damage and percent silk damage of *H. zea*. The amount of silk damage was scored according to visual insect frass amount on the tissues. Percentage leaf damage was scored according to visual assessment of the larval feeding area on 1 inch square leaf cutting. Maize variety B104 and construct 101556 (or construct 109812 for leaf damage) were negative controls from the hybrid cultivar and yellow fluorescent protein (YFP) control respectively, while HX1 was a commercial hybrid Herculex® I, expressing Cry1Fa protein. Construct 109841 was T1 maize expressing the truncated version of the Cry1Da. Data were analyzed by ANOVA and Tukey-Kramer means separation test.

TABLE 7

Percent mortality, percent leaf damage and percent silk damage of *H. zea*.

| Treatment | % Mortality ± SEM* | % Silk Damage ± SEM* | % Leaf Damage ± SEM* |
|---|---|---|---|
| 109841 | 26.79 ± 5.41 (A) | 4.64 ± 1.9(A) | 16.5 ± 0.59 (A) |
| HX1 | 4.17 ± 9.87 (AB) | 39.2 ± 3.47 (B) | 18.9 ± 2.27 (A) |
| 101556 or 109812* | 0 ± 7.65 (B) | 90.78 ± 2.69 (C) | 97.77 ± 2.27 (B) |

TABLE 7-continued

Percent mortality, percent leaf damage and percent silk damage of *H. zea*.

| Treatment | % Mortality ± SEM* | % Silk Damage ± SEM* | % Leaf Damage ± SEM* |
|---|---|---|---|
| B104 | 0 ± 6.46 (B) | 95.01 ± 2.27 (C) | 95.53 ± 2.27(B) |

*Sem = Standard Error of the Mean. Letters in parentheses designate statistical levels. Levels not connected by same letter are significantly different ($P < 0.05$).

*Construct 109812 was the YFP negative control for the leaf damage bioassay.

Example 7

Field Efficacy of Cry1Da Core Toxin Protein Against CEW

Seeds from eight T1 pDAB 109841 transgenic B104 events were tested in field test plots at the DOW AGROSCIENCES Field Station, Fowler, Indiana. These events had been analyzed by molecular techniques as described above and were found to be single copy events having no detectable binary vector backbone sequences. All of the events were tested as $T_1$ plants segregating 1:1 (hemizygous: null) for the Cry1Da/AADI integration event. Negative controls were nontransgenic B104 (Null) plants.

Test plots contained one 20 foot row for each tested insect species. Treatments were planted in a randomized complete block design with four replicates. The experimental entries were treated at the V2 stage with ASSURE® II (DUPONT™ CROP PROTECTION, Wilmington, DE) at 184 gm acid-equivalents per hectare (ae/ha)+1% COC to eliminate the null plants. ASSURE® II contains active ingredient (ai) Quizalofop P-Ethyl Ethyl (R)-2-4-[4-6-chloroquinoxalin-2-yl oxy)-phenoxy]propionate. The commercial product contains 0.88 lb ai per gallon and 1.0% (v/v) crop oil concentrate (COC). COC is an emulsifiable refined paraffinic oil containing about 85% paraffinic oil and about 15% emulsifiers. Stand counts were taken 2 weeks after treatment. Five plants per plot were evaluated for insect damage.

Corn earworm eggs (CEW; *Helicoverpa zea* Boddie) were supplied by BENZON RESEARCH. To assess efficacy against CEW, each plant received 5 second-instar CEW larvae on the silks of ears on 2012 Aug. 21 during flowering (principal growth stage #6). On 2012 Sep. 4, ears were examined for live larvae and feeding damage, determined according to the criteria listed in Table 8.

TABLE 8

Criteria for corm earworm damage assessment.

| Score | Criterion |
|---|---|
| 0 | No damage to silks, husks, cob tip, or kernels |
| 1 | Slight damage to silks or husks only; No cob tip damage or kernels consumed |
| 2 | Moderate damage to silks or husks only; No cob tip damage or kernels consumed |
| 3 | Moderate damage to silks or husks; Slight damage to cob tips, No kernels consumed |
| 4 | Moderate damage to silks, husks, cob tips; Slight damage to kernels, 0.1 to 1.0 cm kernel area consumed (<2 kernels) |
| 5 | Moderate damage to silks, husks, cob tips; Moderate damage to kernels, >1.0 to 2.0 cm of kernel area consumed (3 to 5 kernels) |
| 6 | Heavy damage to silks, husks, cob tips; Moderate damage to kernels, >2.0 to 4.0 cm of kernel area consumed (6 to 10 kernels) |
| 7 | Heavy damage to silks, husks, cob tips; Heavy damage to kernels, >4.0 to 6.0 cm of kernel area consumed (11 to 15 kernels) |
| 8 | Severe damage to silks, husks, cob tips, possibly multiple ear entry locations; Severe damage to kernels, >6.0 to 10.0 cm of kernel area consumed (16 to 25 kernels) |

Quantitative Enzyme Linked Immunosorbant Assays (ELISA) using standard protocols were used to evaluate Cry1Da leaf protein levels in each event. The ELISAs were performed using multiple dilutions of plant extracts and using reagents and instructions essentially as provided by ELISA kit suppliers. Cry1Da antibody as described above was used.

TABLE 9

Results of analytical and insect feeding tests on field-grown plants. Means were separated by the Tukey-Kramer HSD test.

| Plant ID | Leaf Cry1Da ($ng/cm^2$) | CEW No. of Kernels Consumed per Ear | CEW Number of Insects per Ear | CEW Ear Feeding Scale | FAW Foliar Damage |
|---|---|---|---|---|---|
| B104/pDAB109841 {2)021.001 | 135.20 (A)* | 0.36 (C) | 0.08 (C) | 1.28 (C)(D) | 3.90 (B)(C) |
| B104/pDAB109841 {3) 108.001 | 135.13 (A) | 0.00 (C) | 0.00 (C) | 1.00 (D) | 2.00 (D) |
| B104/pDAB109841 {1) 189.001 | 134.75 (A) | 5.15 (C) | 0.29 (C) | 1.97 (C)(D) | 3.80 (B)(C)(D) |
| B104/pDAB109841 {1) 188.001 | 122.15 (A)(B) | 0.00 (C) | 0.05 (C) | 1.03 (D) | 3.40 (B)(C)(D) |
| B104/pDAB109841 {3)116.001 | 107.53 (A)(B)(C) | 0.11 (C) | 0.22 (C) | 1.19 (C)(D) | 2.80 (B)(C)(D) |
| B104/pDAB109841 {1)187.001 | 103.20 (A)(B)(C) | 5.16 (C) | 0.32 (C) | 2.03 (C)(D) | 4.16 (B)(C) |
| B104/pDAB109841 {1)183.001 | 89.58 (B)(C) | 1.62 (C) | 0.08 (C) | 1.42 (C)(D) | 4.07 (B)(C) |
| B104/pDAB109841 {1)185.001 | 67.95 (C) | 0.00 (C) | 0.03 (C) | 1.00 (D) | 4.45 (B) |
| Negative Control Plants | | | | | |
| Null (B104) | N/A | 32.46 (B) | 1.26 (B) | 5.57 (B) | 7.95 (A) |

*Levels not connected by same letter are significantly different.

**N/A = Not Applicable

There was a broad range of Cry1Da accumulation levels, from 67 ng/cm to 135 ng/cm$^2$ All of the pDAB 109841 events tested provided a statistically similar level of protection against CEW, at both the kernel consumption and ear infestation levels, regardless of Cry1Da production level.

REFERENCES

Frankenhuyzen, K. 2009. Minireview: Insecticidal activity of *Bacillus thuringiensis* crystal proteins. Journal of Invertebrate Pathology. 101:1-16.

Karim S., Ridzuddin, S., Gould, F., Dean, D. H. 2000. Determination of Receptor Binding Properties of *Bacillus thuringiensis* δ-Endotoxins to Cotton Bollworm (*Helicoverpa zea*) and Pink Bollworm (*Pectinophora gossypiella*) Midgut Brush Border Membrane Vesicles. Pesticide Biochemistry and Physiology 67 (3): 198-216.

Höfte, H., P. Soetaert, S. Jansens, and M. Peferoen. 1990. Nucleotide sequence and deduced amino acid sequence of a new Lepidoptera-specific crystal protein gene from *Bacillus thuringiensis*. Nucl. Acids Res. 18:5545.

Payne, J., and A. J. Sick. 1997. U.S. Pat. No. 5,691,308.

The invention claimed is:

1. A recombinant polynucleotide operably linked to a heterologous regulatory element, wherein the polynucleotide encodes an insecticidal polypeptide comprising the amino acid sequence of SEQ ID NO: 6, wherein the polynucleotide has codons optimized for expression in an agriculturally important crop.

2. A transgenic plant comprising the polynucleotide of claim 1.

3. A method of controlling a corn earworm insect infestation in a transgenic plant and providing insect resistance management, said method comprising transforming the polynucleotide of claim 1 into a plant.

* * * * *

SEQUENCE LISTING

```
Sequence total quantity: 15
SEQ ID NO: 1            moltype = DNA  length = 3420
FEATURE                 Location/Qualifiers
misc_feature            1..3420
                        note = DIG-911 DNA; Cry1Da2/Cry1Ab chimeric toxin, from
                         pDOW2848
source                  1..3420
                        mol_type = other DNA
                        organism = synthetic construct
SEQUENCE: 1
atggaaataa ataatcaaaa ccaatgtgtg ccttacaatt gtttaagtaa tcctaaggag  60
ataatattag gcgaggaaag gctagaaaca gggaatactg tagcagacat ttcattaggg  120
cttattaatt ttctatattc taattttgta ccaggaggag gatttatagt aggtttacta  180
gaattaatat ggggatttat agggccttcg caatgggata tttttttagc tcaaattgag  240
caattgatta gtcaaagaat agaagaattt gctaggaatc aggcaatttc aagattggag  300
gggctaagca atctttataa ggtctatgtt agagcgttta gcgactggga gaaagatcct  360
actaatcctg ctttaaggga agaaatgcgt atacaattta atgacatgaa tagtgctctc  420
ataacggcta ttccactttt tagagttcaa aattatgaag ttgctctttt atctgtatat  480
gttcaagccg caaacttaca tttatctatt ttaagggatg tttcagtttt cggagaaaga  540
tggggatatg atacagcgac tatcaataat cgctatagtg atctgactag ccttattcat  600
gtttatacta accattgtgt ggatacgtat aatcagggat taaggcgttt ggaaggtcgt  660
tttcttagcg attggattgt atataatcgt ttccggagac aattgacaat ttcagtatta  720
gatattgttg cgttttttcc aaattatgat attagaacat atccaattca aacagctact  780
cagctaacga gggaagtcta tctggattta ccttttatta atgaaaatct ttctcctgca  840
gcaagctatc caacctttc  agctgctgaa agtgctataa ttagaagtcc tcatttagta  900
gactttttaa atagctttac catttataca gatagtctgg cacgttatgc atattgggga  960
gggcacttgg taaattcttt ccgcacagga accactacta atttgataag atccccttta  1020
tatggaaggg aaggaaatac agagcgcccc gtaactatta ccgcatcacc tagcgtacca  1080
atatttagaa cactttcata tattacaggc cttgacaatt caaatcctgt agctggaatc  1140
gagggagtgg aattccaaaa tactataagt agaagtatct atcgtaaaag cggtccaata  1200
gattctttta gtgaattacc acctcaagat gccagcgtat ctcctgcaat tgggtatagt  1260
caccgtttat gccatgcaac atttttagaa cggattagtg gaccaagaat agcaggcacc  1320
gtattttctt ggacacaccg tagtgccagc cctactaatg aagtaagtcc atctagaatt  1380
acacaaattc catgggtaaa ggcgcatact cttgcatctg gtgcctccgt cattaaaggt  1440
cctggattta caggtggaga tattctgact aggaatagta tgggcgagct ggggacctta  1500
cgagtaacct tcacaggaag attaccacaa agttattata tacgtttccg ttatgcttcg  1560
gtagcaaata ggagtggtac atttagatat tcacagccac cttcgtatgg aatttcattt  1620
ccaaaaacta tggacgcagg tgaaccacta acatctcgtt cgttcgctca tacaacactc  1680
ttcactccaa taacctttc  acgagctcaa gaagaatttg atctatacat ccaatcgggt  1740
gtttatatag atcgaattga atttataccg gttactgcaa cactggaggc agagtctgac  1800
ttggaaagag cacagaaggc ggtgaatgct ctgttcactt cgtccaatca gattgggctc  1860
aagacagatg tgactgacta tcacatcgat cgcgtttcca accttgttga gtgcctctct  1920
gatgagttct gtttggatga gaagaaggag ttgtccgaga aggtcaaaca tgctaagcga  1980
cttagtgatg agcggaactt gcttcaagat cccaactttc gcgggatcaa caggcaacta  2040
gatcgtggat ggaggggaag tacggacatc accattcaag gaggtgatga tgtgttcaag  2100
gagaactatg ttacgctctt gggtaccttt gatgagtgct atccaacata cctgtaccag  2160
aagatagatg aatcgaaact caaagcctac acaagatacc agttgagagg ttacatcgag  2220
gacagtcaag accttgagat ctacctcatc agatacaacg ccaaacatga gacagtcaat  2280
gtgcctggga cgggttcact ctggccactt tcagccccaa gtcccatcgg caagtgtgcc  2340
catcactcac accacttctc cttggacata gacgttggct gtaccgacct gaacgaagac  2400
ctcggtgtgt gggtgatctt caagatcaag actcaagatg gccatgccag gctaggcaat  2460
ctggagtttc tagaagagaa accacttgtt ggagaagccc tcgctagagt gaagagggct  2520
gagaagaagt ggagggacaa gagagagaag ttggaatggg aaacaaacat tgtgtacaaa  2580
gaagccaaag aaagcgttga cgctctgttt gtgaactctc agtatgatag gctccaagct  2640
gataccaaca tagctatgat tcatgctgca gacaaacgcg ttcatagcat tcgggaagct  2700
taccttcctg aacttagcgt gattccgggt gtcaatgctg ctatctttga agagttagaa  2760
gggcgcatct tcactgcatt ctccttgtat gatgcgagga atgtcatcaa gaatggtgac  2820
ttcaacaatg gcctatcctg ctggaatgtg aaagggcacg tagatgtaga agaacagaac  2880
aatcaccgct ctgtccttgt tgttcctgag tgggaagcag aagtttcaca agaagttcgt  2940
gtctgtcctg gtcgtggcta cattcttcgt gttaccgcgt acaaagaagg atacggagaa  3000
ggttgcgtca ccatacacga gattgagaac aacaccgacg agctgaagtt cagcaactgc  3060
gtcgaggagg aagtctaccc aaacaacacc gtaacttgca atgactacac tgcgactcaa  3120
gaggagtatg agggtactta cacttctcgc aatcgaggat acgatggagc ctatgagagc  3180
```

-continued

```
aactcttctg tacccgctga ctatgcatca gcctatgagg agaaggctta caccgatgga  3240
cgtagggaca atccttgcga atctaacaga ggctatgggg actacacacc gttaccagcc  3300
ggctatgtca ccaaagagtt agagtacttt ccagaaaccg acaaggtttg gattgagatt  3360
ggagaaacgg aaggaacatt cattgttgat agcgtggagt tacttctgat ggaggaatga  3420

SEQ ID NO: 2            moltype = AA  length = 1139
FEATURE                 Location/Qualifiers
REGION                  1..1139
                        note = amino acid sequence for the DIG-911 protein
                         (Cry1Da2/Cry1Abchimeric insecticidal toxin, which consists
                         of a core toxinsegment of Cry1Da (amino acids 1 to 594, as
                         disclosed in GENBANKAccession No. 176415.1 and U.S Patent
                         No. 5,691,308) and a
source                  1..1139
                        mol_type = protein
                        organism = synthetic construct
SEQUENCE: 2
MEINNQNQCV PYNCLSNPKE IILGEERLET GNTVADISLG LINFLYSNFV PGGGFIVGLL  60
ELIWGFIGPS QWDIFLAQIE QLISQRIEEF ARNQAISRLE GLSNLYKVYV RAFSDWEKDP  120
TNPALREEMR IQFNDMNSAL ITAIPLFRVQ NYEVALLSVY VQAANLHLSI LRDVSVFGER  180
WGYDTATINN RYSDLTSLIH VYTNHCVDTY NQGLRRLEGR FLSDWIVYNR FRRQLTISVL  240
DIVAFFPNYD IRTYPIQTAT QLTREVYLDL PFINENLSPA ASYPTFSAAE SAIIRSPHLV  300
DFLNSFTIYT DSLARYAYWG GHLVNSFRTG TTTNLIRSPL YGREGNTERP VTITASPSVP  360
IFRTLSYITG LDNSNPVAGI EGVEFQNTIS RSIYRKSGPI DSFSELPPQD ASVSPAIGYS  420
HRLCHATFLE RISGPRIAGT VFSWTHRSAS PTNEVSPSRI TQIPWVKAHT LASGASVIKG  480
PGFTGGDILT RNSMGELGTL RVTFTGRLPQ SYYIRFRYAS VANRSGTFRY SQPPSYGISF  540
PKTMDAGEPL TSRSFAHTTL FTPITFSRAQ EEFDLYIQSG VYIDRIEFIP VTATLEAESD  600
LERAQKAVNA LFTSSNQIGL KTDVTDYHID RVSNLVECLS DEFCLDEKKE LSEKVKHAKR  660
LSDERNLLQD PNFRGINRQL DRGWRGSTDI TIQGGDDVFK ENYVTLLGTF DECYPTYLYQ  720
KIDESKLKAY TRYQLRGYIE DSQDLEIYLI RYNAKHETVN VPGTGSLWPL SAPSPIGKCA  780
HHSHHFSLDI DVGCTDLNED LGVWVIFKIK TQDGHARLGN LEFLEEKPLV GEALARVKRA  840
EKKWRDKREK LEWETNIVYK EAKESVDALF VNSQYDRLQA DTNIAMIHAA DKRVHSIREA  900
YLPELSVIPG VNAAIFEELE GRIFTAFSLY DARNVIKNGD FNNGLSCWNV KGHVDVEEQN  960
NHRSVLVVPE WEAEVSQEVR VCPGRGYILR VTAYKEGYGE GCVTIHEIEN NTDELKFSNC  1020
VEEEVYPNNT VTCNDYTATQ EEYEGTYTSR NRGYDGAYES NSSVPADYAS AYEEKAYTDG  1080
RRDNPCESNR GYGDYTPLPA GYVTKELEYF PETDKVWIEI GETEGTFIVD SVELLLMEE   1139

SEQ ID NO: 3            moltype = DNA  length = 3447
FEATURE                 Location/Qualifiers
misc_feature            1..3447
                        note = DIG-180 DNA; Cry1Fa2
source                  1..3447
                        mol_type = other DNA
                        organism = synthetic construct
SEQUENCE: 3
atggaaaata atattcaaaa tcaatgcgta ccttacaatt gtttaaataa tcctgaagta  60
gaaatactga acgaagaacg cagcaccggc cgcctgccgc tggacatcag cctgagcctt  120
acacgtttcc ttttgagtga atttgttcca ggtgtgggag ttgcgtttgg attatttgat  180
ttaatatggg gttttataac tccttctgat tggagcttat ttcttttaca gattgaacaa  240
ttgattgagc aaagaataga aacattggaa aggaaccggg caattactac attacgaggg  300
ttagcagata gctatgaaat ttatattgaa gcactaagag agtgggaagc aaatcctaat  360
aatgcacaat taagggaaga tgtgcgtatt cgatttgcta atacagacga cgctttaata  420
acagcaataa ataattttac acttacaagt tttgaaatcc ctcttttatc ggtctatgtt  480
caagcggcga atttacattt atcactatta agagacgcag tatcgtttgg gcagggttgg  540
ggactggata tagctactgt taataatcat tataatagat taataaatct tattcataga  600
tatacgaaac attgtttgga cacatacaat caaggattag aaaacttaag aggtactaat  660
actcgacaat gggcaagatt caatcagttt aggagagatt taacacttac tgtattagat  720
atcgttgctc tttttccgaa ctacgatgtt agaacatatc caattcaaac gtcatcccaa  780
ttaacaaggg aaatttatac aagttcagta attgaggatt ctccagtttc tgctaatata  840
cctaatggtt ttaatagggc ggaatttgga gttagaccgc cccatcttat ggactttatg  900
aattctttgt ttgtaactgc agagactgtt agaagtcaaa ctgtgtgggg aggacactta  960
gttagttcac gaaatacggc tggtaaccgt ataaatttcc ctagttacgg ggtcttcaat  1020
cctggtggcg ccatttggat tgcagatgag gatccacgtc ctttttatcg gacattatca  1080
gatcctgttt ttgtccgagg aggatttggg aatcctcatt atgtactggg gcttagggga  1140
gtagcatttc aacaaactgg tacgaaccac acccgaacat ttagaaatag tgggaccata  1200
gattctctag atgaaatccc acctcaggat aatagtgggg caccttggaa tgattatagt  1260
catgtattaa atcatgttac atttgtacga tggccaggtg agatttcagg aagtgattca  1320
tggagagctc caatgttttc ttggacgcac cgtagtgcaa cccctacaaa tacaattgat  1380
ccggagagga ttactcaaat accattggta aaagcacata cacttcagtc aggtactact  1440
gttgtaagag ggcccgggtt tacgggagga gatattcttc gacgaacaag tggaggacca  1500
tttgcttata ctattgttaa tataaatggg caattacccc aaaggtatcg tgcaagaata  1560
cgctatgcct ctactacaaa tctaagaatt tacgtaacgg ttgcaggtga acggattttt  1620
gctggtcaat ttaacaaaac aatggatacc ggtgacccat taacattcca atcttttagt  1680
tacgcaacta ttaatacagc ttttacattc ccaatgagcc agagtagttt cacagtaggt  1740
gctgatactt ttagttcagg gaatgaagtt tatatagaca gatttgaatt gattccagtt  1800
actgcaacat tggaagcaga atctgattta gaaagagcac aaaaggcggt gaatgcgctg  1860
tttacttcta gcaaccaaat agggctaaaa acagatgtga cggattatca tatcgatcga  1920
gtatccaatt tagttgagtg tttatctgat gaattttgtc tggatgaaaa aaaagaattg  1980
tccgagaaag tcaaacatgc gaagcgactt agtgatgagc ggaatttact tcaagatcca  2040
```

-continued

```
aactttagag ggatcaatag acaactagac cgtggctgga gaggaagtac ggatattacc  2100
atccaaggag gcgatgacgt attcaaagag aattacgtta cgctattggg tacctttgat  2160
gagtgctatc caacgtattt atatcaaaaa atagatgagt cgaaattaaa agcctatacc  2220
cgttaccaat taagagggta tatcgaagat agtcaagact tagaaatcta tttaattcgc  2280
tacaatgcca aacacgaaac agtaaatgtg ccaggtacgg gttccttatg gccgctttca  2340
gccccaagtc caatcggaaa atgtgcccat cattcccatc atttctcctt ggacattgat  2400
gttggatgta cagacttaaa tgaggactta ggtgtatggg tgatattcaa gattaagacg  2460
caagatggcc atgcaagact aggaaatcta gaatttctcg aagagaaacc attagtagga  2520
gaagcactag ctcgtgtgaa aagagcggag aaaaaatgga gagacaaacg tgaaaaattg  2580
gaatgggaaa caaatattgt ttataaagag gcaaaagaat ctgtagatgc tttatttgta  2640
aactctcaat atgatagatt acaagcggat accaacatcg cgatgattca tgcggcagat  2700
aaacgcgttc atagcattcg agaagcttat ctgcctgagc tgtctgtgat tccgggtgtc  2760
aatgcggcta tttttgaaga attagaaggg cgtattttca ctgcattctc cctatatgat  2820
gcgagaaatg tcattaaaaa tggtgatttt aataatggct tatcctgctg gaacgtgaaa  2880
gggcatgtag atgtagaaga acaaaacaac caccgttcgg tccttgttgt tccggaatgg  2940
gaagcagaag tgtcacaaga agttcgtgtc tgtccgggtc gtggctatat ccttcgtgtc  3000
acagcgtaca aggagggata tggagaaggt tgcgtaacca ttcatgagat cgagaacaat  3060
acagacgaac tgaagtttag caactgtgta gaagaggaag tatatccaaa caacacggta  3120
acgtgtaatg attatactgc gactcaagaa gaatatgagg gtacgtacac ttctcgtaat  3180
cgaggatatg acggagccta tgaaagcaat tcttctgtac cagctgatta tgcatcagcc  3240
tatgaagaaa aagcatatac agatggacga agagacaatc cttgtgaatc taacagagga  3300
tatggggatt acacaccact accagctggc tatgtgacaa aagaattaga gtacttccca  3360
gaaaccgata aggtatggat tgagatcgga gaaacggaag gaacattcat cgtggacagc  3420
gtggaattac ttcttatgga ggaataa                                    3447

SEQ ID NO: 4            moltype = AA  length = 1148
FEATURE                 Location/Qualifiers
REGION                  1..1148
                        note = DIG-180 protein; Cry1Fa2
source                  1..1148
                        mol_type = protein
                        organism = synthetic construct
SEQUENCE: 4
MENNIQNQCV PYNCLNNPEV EILNEERSTG RLPLDISLSL TRFLLSEFVP GVGVAFGLFD  60
LIWGFITPSD WSLFLLQIEQ LIEQRIETLE RNRAITTLRG LADSYEIYIE ALREWEANPN  120
NAQLREDVRI RFANTDDALI TAINNFTLTS FEIPLLSVYV QAANLHLSLL RDAVSFGQGW  180
GLDIATVNNH YNRLINLIHR YTKHCLDTYN QGLENLRGTN TRQWARFNQF RRDLTLTVLD  240
IVALFPNYDV RTYPIQTSSQ LTREIYTSSV IEDSPVSANI PNGFNRAEFG VRPPHLMDFM  300
NSLFVTAETV RSQTVWGGHL VSSRNTAGNR INFPSYGVFN PGGAIWIADE DPRPFYRTLS  360
DPVFVRGGFG NPHYVLGLRG VAFQQTGTNH TRTFRNSGTI DSLDEIPPQD NSGAPWNDYS  420
HVLNHVTFVR WPGEISGSDS WRAPMFSWTH RSATPTNTID PERITQIPLV KAHTLQSGTT  480
VVRGPGFTGG DILRRTSGGP FAYTIVNING QLPQRYRARI RYASTTNLRI YVTVAGERIF  540
AGQFNKTMDT GDPLTFQSFS YATINTAFTF PMSQSSFTVG ADTFSSGNEV YIDRFELIPV  600
TATLEAESDL ERAQKAVNAL FTSSNQIGLK TDVTDYHIDR VSNLVECLSD EFCLDEKKEL  660
SEKVKHAKRL SDERNLLQDP NFRGINRQLD RGWRGSTDIT IQGGDDVFKE NYVTLLGTFD  720
ECYPTYLYQK IDESKLKAYT RYQLRGYIED SQDLEIYLIR YNAKHETVNV PGTGSLWPLS  780
APSPIGKCAH HSHHFSLDID VGCTDLNEDL GVWVIFKIKT QDGHARLGNL EFLEEKPLVG  840
EALARVKRAE KKWRDKREKL EWETNIVYKE AKESVDALFV NSQYDRLQAD TNIAMIHAAD  900
KRVHSIREAY LPELSVIPGV NAAIFEELEG RIFTAFSLYD ARNVIKNGDF NNGLSCWNVK  960
GHVDVEEQNN HRSVLVVPEW EAEVSQEVRV CPGRGYILRV TAYKEGYGEG CVTIHEIENN  1020
TDELKFSNCV EEEVYPNNTV TCNDYTATQE EYEGTYTSRN RGYDGAYESN SSVPADYASA  1080
YEEKAYTDGR RDNPCESNRG YGDYTPLPAG YVTKELEYFP ETDKVWIEIG ETEGTFIVDS  1140
VELLLMEE                                                         1148

SEQ ID NO: 5            moltype = DNA  length = 1812
FEATURE                 Location/Qualifiers
misc_feature            1..1812
                        note = Cry1Da2 v4 DNA from pDAB109841 (truncated Cry1Da;
                         maizeoptimized)
source                  1..1812
                        mol_type = other DNA
                        organism = synthetic construct
SEQUENCE: 5
atggagatca acaaccagaa tcagtgcgtt ccttacaact gtctgagcaa ccccaaagaa  60
atcatccttg gcgaggagag gctggaaact ggcaacacag tggctgacat tagcttgggt  120
cttatcaact tcttgtactc aaactttgtt cccggtggag gcttcattgt gggactgctt  180
gagctgatat ggggtttcat aggtccgagc cagtgggaca tctttctggc acaaatcgag  240
cagctcatct cacagcggat tgaggagttt gcgagaaatc aagccatatc gagactcgaa  300
gggctgtcca acttgtacaa ggtctatgtg agggctttct ctgattggga gaaggacccc  360
acgaatccag cgcttcgcga ggagatgagg atacagttca atgacatgaa ctctgcgttg  420
atcacggcta ttccgctctt tagggtgcag aactacgagg ttgctctgct ctcagtgtac  480
gtgcaagctg ccaacttgca tctgagcatc ctccgggacg tctcggtgtt tggggaacgg  540
tggggttatg acaccgcaac gatcaacaac cgctattcag accttacatc tcttatccac  600
gtgtacacga atcactgcgt tgatacgtac aatcaaggcc tccgcagact cgaagggagg  660
ttcctcagcg attggattgt ttacaatcgc ttcagacggc aactcacaat ctcggttctg  720
gacatagtcg cgttcttccc gaactatgat atccgcacct atcccattca gaccgctact  780
cagctcactc gcgaagtgta tcttgacctc ccgttcatca atgagaactt gtcaccagca  840
gcgtcctatc ccaccttctc agctgcggag tccgctatca tccgctcccc acatctggtt  900
gatttcctca actctttcac tatctacacc gactcgcttg cgagatacgc atactggggt  960
```

-continued

```
ggccatctgg tgaactcatt ccggactggc accacgacca atctgatccg cagccctctc  1020
tacggacgcg agggcaacac cgagaggcca gtgaccatca ccgcttcccc ttccgttcct  1080
atcttccgca ccctttcgta cattactggc ctcgacaaca gcaacccagt cgctggcatc  1140
gagggtgttg agtttcagaa caccatttct aggtctatct ataggaagag cggtccaata  1200
gactcgtttt ctgagttgcc tccccaagat gcctctgtca gcccagccat tggctactcc  1260
catcggctct gtcacgccac cttccttgaa cgcatctccg gaccaaggat cgctgggacg  1320
gtctttagct ggacccaccg ctcagcatct ccgacaaatg aggtctcccc ttcccgcatc  1380
acacaaatcc cgtgggtgaa ggcacacaca ttggcctcgg gagcctcggt catcaaaggg  1440
cctggcttca ctggaggcga cattctgacg aggaactcaa tgggtgagct ggggaccttg  1500
agggtcactt tcactggacg cctcccacag tcctactaca ttcggttccg ctatgccagc  1560
gtggccaata ggtccggaac attccgctac agccagccac ccagctacgg cattagcttc  1620
cctaagacta tggatgctgg ggaacctctg acctcaaggt cgtttgccca cacgacgctg  1680
ttcaccccta tcacattcag cagagcacaa gaggagtttg atctgtacat ccagtccgga  1740
gtctacattg accggatcga gttcattccg gttactgcga cactcgaggc tgaatcggat  1800
cttgaaaggt ga                                                      1812

SEQ ID NO: 6           moltype = AA  length = 603
FEATURE                Location/Qualifiers
REGION                 1..603
                       note = Cry1Da2 v4 protein (truncated Cry1Da)
source                 1..603
                       mol_type = protein
                       organism = synthetic construct
SEQUENCE: 6
MEINNQNQCV PYNCLSNPKE IILGEERLET GNTVADISLG LINFLYSNFV PGGGFIVGLL  60
ELIWGFIGPS QWDIFLAQIE QLISQRIEEF ARNQAISRLE GLSNLYKVYV RAFSDWEKDP  120
TNPALREEMR IQFNDMNSAL ITAIPLFRVQ NYEVALLSVY VQAANLHLSI LRDVSVFGER  180
WGYDTATINN RYSDLTSLIH VYTNHCVDTY NQGLRRLEGR FLSDWIVYNR FRRQLTISVL  240
DIVAFFPNYD IRTYPIQTAT QLTREVYLDL PFINENLSPA ASYPTFSAAE SAIIRSPHLV  300
DFLNSFTIYT DSLARYAYWG GHLVNSFRTG TTTNLIRSPL YGREGNTERP VTITASPSVP  360
IFRTLSYITG LDNSNPVAGI EGVEFQNTIS RSIYRKSGPI DSFSELPPQD ASVSPAIGYS  420
HRLCHATFLE RISGPRIAGT VFSWTHRSAS PTNEVSPSRI TQIPWVKAHT LASGASVIKG  480
PGFTGGDILT RNSMGELGTL RVTFTGRLPQ SYYIRFRYAS VANRSGTFRY SQPPSYGISF  540
PKTMDAGEPL TSRSFAHTTL FTPITFSRAQ EEFDLYIQSG VYIDRIEFIP VTATLEAESD  600
LER                                                                603

SEQ ID NO: 7           moltype = DNA  length = 20
FEATURE                Location/Qualifiers
misc_feature           1..20
                       note = AAD1F Primer
source                 1..20
                       mol_type = other DNA
                       organism = synthetic construct
SEQUENCE: 7
tgttcggttc cctctaccaa                                              20

SEQ ID NO: 8           moltype = DNA  length = 22
FEATURE                Location/Qualifiers
misc_feature           1..22
                       note = AAD1R Primer
source                 1..22
                       mol_type = other DNA
                       organism = synthetic construct
SEQUENCE: 8
caacatccat caccttgact ga                                           22

SEQ ID NO: 9           moltype = DNA  length = 24
FEATURE                Location/Qualifiers
misc_feature           1..24
                       note = AAD1P Probe
source                 1..24
                       mol_type = other DNA
                       organism = synthetic construct
SEQUENCE: 9
cacagaaccg tcgcttcagc aaca                                         24

SEQ ID NO: 10          moltype = DNA  length = 19
FEATURE                Location/Qualifiers
misc_feature           1..19
                       note = SPC1A Primer
source                 1..19
                       mol_type = other DNA
                       organism = synthetic construct
SEQUENCE: 10
cttagctgga taacgccac                                               19

SEQ ID NO: 11          moltype = DNA  length = 19
FEATURE                Location/Qualifiers
misc_feature           1..19
```

-continued

```
                          note = SPC1S Primer
source                    1..19
                          mol_type = other DNA
                          organism = synthetic construct
SEQUENCE: 11
gaccgtaagg cttgatgaa                                              19

SEQ ID NO: 12             moltype = DNA  length = 21
FEATURE                   Location/Qualifiers
misc_feature              1..21
                          note = TQSPC Probe
source                    1..21
                          mol_type = other DNA
                          organism = synthetic construct
SEQUENCE: 12
cgagattctc cgcgctgtag a                                           21

SEQ ID NO: 13             moltype = DNA  length = 18
FEATURE                   Location/Qualifiers
misc_feature              1..18
                          note = InvertaseF Primer
source                    1..18
                          mol_type = other DNA
                          organism = synthetic construct
SEQUENCE: 13
tggcggacga cgacttgt                                               18

SEQ ID NO: 14             moltype = DNA  length = 19
FEATURE                   Location/Qualifiers
misc_feature              1..19
                          note = InvertaseR Primer
source                    1..19
                          mol_type = other DNA
                          organism = synthetic construct
SEQUENCE: 14
aaagtttgga ggctgccgt                                              19

SEQ ID NO: 15             moltype = DNA  length = 21
FEATURE                   Location/Qualifiers
misc_feature              1..21
                          note = InvertaseP Probe
source                    1..21
                          mol_type = other DNA
                          organism = synthetic construct
SEQUENCE: 15
cgagcagacc gccgtgtact t                                           21
```